(12) United States Patent
Shmulevich et al.

(10) Patent No.: US 7,257,563 B2
(45) Date of Patent: Aug. 14, 2007

(54) PROBABILISTIC BOOLEAN NETWORKS

(75) Inventors: Ilya Shmulevich, Houston, TX (US); Edward R. Dougherty, College Station, TX (US); Wei Zhang, Houston, TX (US)

(73) Assignees: The Board of Regents of The University of Texas, Austin, TX (US); The Texas A&M University System, College Station, TX (US)

( * ) Notice: Subject to any disclaimer, the term of this patent is extended or adjusted under 35 U.S.C. 154(b) by 593 days.

(21) Appl. No.: 10/354,907

(22) Filed: Jan. 30, 2003

(65) Prior Publication Data

US 2003/0225718 A1 Dec. 4, 2003

Related U.S. Application Data

(60) Provisional application No. 60/352,725, filed on Jan. 30, 2002.

(51) Int. Cl.
- G06E 1/00 (2006.01)
- G06E 3/00 (2006.01)
- G06F 15/18 (2006.01)
- G06G 7/00 (2006.01)
- G06N 3/02 (2006.01)

(52) U.S. Cl. ........................................................ 706/15
(58) Field of Classification Search .................. 706/15
See application file for complete search history.

(56) References Cited

U.S. PATENT DOCUMENTS 6,169,981 B1    1/2001    Werbos ....................... 703/23

| | | | |
|---|---|---|---|
| 2002/0042786 A1 | 4/2002 | Scarborough et al. | 706/21 |
| 2002/0046199 A1 | 4/2002 | Scarborough et al. | 706/21 |
| 2003/0130973 A1* | 7/2003 | Sumner et al. | 706/45 |

OTHER PUBLICATIONS

Learning by probabilistic Boolean networks, Dorigo, M.; Neural Networks, 1994. IEEE World Congress on Computational Intelligence., IEEE International Conference on pp. 887-891 vol. 2 Digital Object Identifier 10.1109/ICNN.1994.374297.*

Datta et al., "External control in Markovian genetic regulatory networks," (to appear in) *Machine Learning.*, pp. 1-25.

Dougherty and Shmulevich, "Mappings between probabilistic Boolean networks," *Signal Processing*, 83:799-809, 2003.

Dougherty et al., "Coefficient of determination in nonlinear signal processing," *Signal Processing*, 80:2219-2235, 2000.

(Continued)

*Primary Examiner*—Anthony Knight
*Assistant Examiner*—Michael B. Holmes
(74) *Attorney, Agent, or Firm*—Fulbright & Jaworski L.L.P.

(57) ABSTRACT

Embodiments of the invention encompass methods for modeling of complex systems, which include, but are not limited to gene regulatory networks, biological systems, and the like. Other embodiments of the invention include the development of computational tools for the identification and discovery of potential targets for therapeutic intervention in diseases such as cancer. The embodiments discussed utilize methods that model the potential effect of individual genes on the global dynamical network behavior, both from the view of random gene mutation as well as intervention in order to elicit desired network behavior.

21 Claims, 13 Drawing Sheets

OTHER PUBLICATIONS

Hashimoto et al., "Efficient selection of feature sets possessing high coefficients of determination based on incremental determinations," *Signal Processing*, 83(4):695-712, 2003.

Kim et al., "Can Markov chain models mimic biological regulation?" *J. Biol. Sys.*, 10:337-357, 2002.

Kim et al., "General nonlinear framework for the analysis of gene interaction via multivariate expression arrays," *J. Biomed. Optics*, 5(4):411-424, 2000.

Kim et al., "Multivariate measurement of gene expression relationships," *Genomics*, 67:201-209, 2000.

Lähdesmäki et al., "On learning gene regulatory networks under the boolean network system," *Machine Learning*, 17(36):1-26, 2002.

Melnik et al., "Block-Median Pyramidal Transform: Analysis and Denoising Applications," *IEEE Transactions on Signal Processing*, 49(2):364-372, 2001.

Shmulevich et al., "Control of stationary behavior in probabilistic Boolean networks by means of structural intervention," *J. Biol. Sys.*, 10:431-445, 2002.

Shmulevich et al., "From Bolean to probabilistic Boolean networks as models of genetic regulatory networks," *Proceedings of the IEEE*, 90:1778-1792, 2002.

Shmulevich et al., "Gene pertubation and intervention in probabilistic Boolean networks," *Bioinformatics*, 18:1319-1331, 2002.

Shmulevich et al., "Inference of genetic regulatory networks via best-fit extensions," in: *Computational and Statistical Approaches to Genomics*, Zhang and Shmulevich (eds.), Chapter 11: pp. 197-210, 2002.

Shmulevich et al., "Probabilistic Boolean networks: a rule-based uncertainty model for gene regulatory networks," *Bioinformatics*, 18:261-274, 2002.

Suh et al., "Parallel computation and visualization tools for codetermination analysis of multivariate gene-expression relations," in: *Computational and Statistical Approaches to Genomics*, Zhang and Shmulevich (eds.), chapter 13: pp. 227-240, 2002.

Tabus and Astola, "On the use of MDL principle in gene expression prediction," *J. of Applied Signal Processing*, 2001(4):297-303, 2001.

Tabus et al., "Normalized maximum likelihood models for Boolean regression with application to prediction and classification in genomics," in: *Computational and Statistical Approaches to Genomics*, Zhang and Shmulevich (eds.), Chapter 10: pp. 173-196, 2002.

Watts and Strogatz, "Collective dynamics of 'small-world' networks," *Nature*, 393(6684):440-442, 1998.

Zhou et al., "Construction of genomic networks using mutual-information clustering and reversible-jump Markov-chain-Monte-Carlo predictor design," *Signal Processing*, 83:745-761, 2003.

Fox and Furmanski, "Load balancing loosely synchronous problems with a neural network," *ACM Hypercube Concurrent Computers and Applications*, pp. 241-278, Feb. 1988.

Jimenez and Lin, "Dynamic branch prediction with perceptrons," Technical Report TR2000-08, Dept. of Computer Sciences, The University of Texas, pp. 1-10, 2000.

Jimenez and Lin, "Neural methods for dynamic branch prediction," *ACM Transactions on Computer Systems*, 20(4):369-397, 2002.

Jimenez et al., "Boolean formula-based branch prediction for future technologies," *Proceedings of the International Conference on Parallel Architectures and Compilation Techniques*, pp. 1-10, Sep. 2001.

Jimenez et al., "The Impact of delay on the design of branch predictors," *Proceedings of the 33rd Annual International Symposium on Microarchitecture*, pp. 1-10, Dec. 2000.

Mulgund et al., "OLIPSA: on-line intelligent processor for situation assessment," *2nd Annual Symposium and Exhibiton on Situational Awareness in the Tactical Air Environment*, pp. 1-13, Jun. 1997.

Reese et al., "Improved splice site detection in genie," *ACM Annual Conference on Research in Computational Molecular Biology*, pp. 232-240, 1997.

Schrodt, "Machine Learning," Chapter 5 in: *Patterns Rules and Learning*, Version 1.0, 1-76, 1995.

\* cited by examiner

State transition diagram corresponding to the PBN in Example 1.

Steady-state distribution of the Markov chain corresponding to the PBN given in Example 1, with $p = 0.01$.

A diagram illustrating the cell cycle regulation example. Arrowed lines represent activation and lines with bars at the end represent inhibition.

The logic diagram describing the activity of Rb protein in terms of 4 inputs: cdk7, cyclin H, cyclin E, and p21. The gate with inputs cdk7 and cyclin H is an AND gate, the gate with input p21/WAF1 is a NOT gate, and the gate whose output is Rb is a NAND (negated AND) gate.

An example of a wiring diagram for $n = 3$.

State transition diagram of an independent PBN without a steady-state distribution.

Example of a dependent PBN not containing a steady-state distribution.

PROBABILISTIC BOOLEAN NETWORKS

This application claims priority to U.S. Provisional Patent application Ser. No. 60/352,725 filed Jan. 30, 2002 and is incorporated herein by reference.

FIELD OF THE INVENTION

The present invention relates generally to methods of establishing and modeling a regulatory relationship between nodes of a network, and more particularly to establishing and modeling a regulatory relationship between nodes of a biological network using Probabilistic Boolean Networks.

BACKGROUND OF THE INVENTION

The near-completion of the Human Genome Projects has revealed that there are approximately 30,000 to 40,000 genes in the human genome. Genetic and molecular studies have shown that each gene may be linked to other genes at various levels, such as transcriptional regulation and protein interactions. In this new era of genomic biology, single gene or protein perspectives are becoming increasingly limited for gaining insight into biological processes. Global, systemic, or network perspectives are becoming increasingly important for making progress in our understanding of the biological processes and harnessing this understanding in educated intervention for correcting human diseases. The development of high throughput genomic and proteomic technologies is empowering researchers in the collection of broad-scope gene information. However, it remains a major challenge to digest the massive amounts of information and use it in an intelligent and comprehensive manner. The development of systematic approaches to finding genes for effective therapeutic intervention requires new models and tools for understanding and managing complex genetic networks.

To understand the nature of cellular function, it is necessary to study the behavior of genes in a holistic rather than in an individual manner. Mathematical and computational methods may be developed to construct formal models of genetic interactions. This research direction provides insight and a conceptual framework for an integrative view of genetic function and regulation.

There have been a number of attempts to model gene regulatory networks, including linear models, Bayesian network models, neural network models, differential equation-based models, and models including stochastic components on the molecular level. In general, gene expression time trajectories can be modeled as random functions of time. The model system that has received, perhaps, the most attention is the Boolean Network model originally introduced in the late 1960's to early 1970's. In this model, gene expression is quantized to only two levels: ON and OFF. The expression level (state) of each gene is functionally related to the expression states of some other genes, using logical rules. Computational methods that reveal these logical inter-relations have been successfully constructed.

Recent computational methods indicate that many other realistic biological questions may be answered within the seemingly simplistic Boolean formalism, which emphasizes fundamental, generic principles rather than quantitative biochemical details. Current methods have yielded insights into the overall behavior of large genetic networks and allow the study of large data sets in a global fashion. For example, the dynamic behavior of such networks can be used to model many biologically meaningful phenomena, for example, cellular state dynamics, possessing switch-like behavior, stability, and hysteresis. Additional uses of such methods may include uses such as the identification of suitable drug targets in cancer therapy by inferring the structure of the genetic models from experimental data (e.g., from gene expression profiles). Recent work has gone into identifying the structure of gene regulatory networks from expression data. It remains an open question as to the degree to which the Boolean formalism can explain the complicated genetic network interplay of higher-order eukaryotes, where more uncertainty of the network exists, attributed to increased gene complexity and differentiation-related specification.

Other methods depart from traditional deterministic constraints of Boolean models by using so-called noisy Boolean networks together with an identification algorithm, in order to deal with noise present in expression patterns. In that model, the requirement of consistency intrinsically imposed by Boolean functions are relaxed.

Limitations of standard Boolean networks include an inherent determinism. From a conceptual point of view, it is likely that the regularity of genetic function and interaction known to exist is not due to hard-wired logical rules, but rather to the intrinsic self-organizing stability of the dynamical system, despite the existence of stochastic components in the cell. Empirically, the assumption of only one logical rule per gene may lead to incorrect conclusions when inferring these rules from gene expression measurements, as the latter are typically noisy and the number of samples is small relative to the number of parameters to be inferred.

SUMMARY OF THE INVENTION

Certain embodiments of the invention include methods based on a new class of models called Probabilistic Boolean Networks (PBNs), which are probabilistic generalizations of a standard Boolean network that offer a flexible and powerful modeling framework. PBNs share the appealing properties of Boolean networks in that they incorporate rule-based dependencies between nodes of a network and allow systematic study of global network dynamics. However, because of their probabilistic nature, they are able to cope with uncertainty, which is intrinsic to complex systems. PBNs typically provide a natural way to quantify the relative influence and sensitivity of network nodes (e.g., factors that influence gene expression/activity, protein activity, etc.) in their interactions with other network nodes.

FIG. 1 illustrates a building block (cluster) 110 of an exemplary network. A network may consist of one or more building blocks 110, as illustrated in FIG. 1 by a subscript n outside the outermost brackets. In certain embodiments, sub-clusters may be further organized into higher order or multilevel networks, e.g., meta-clusters. Sub-clusters is a sub-population of with demonstrable or close interaction. The building block 110 comprises input nodes 111 (e.g., factors that influence the system) that are typically supplied to predictor functions 113, which may be inferred from network data. Input nodes 111 may be values supplied by a) measurement of various factors that influence the value a node(s) in the network, b) an output of another building block of the PBN (e.g., other nodes that may be the target node of another building block), or c) combinations thereof. Predictor functions 113 may be inferred from input nodes 111, for example, predictor functions 113 may be derived from a) the relationship between nodes with a particular cumulative measures of association (e.g., coefficient of determination (COD) between one or more combination(s) of network nodes), b) predetermined associations of network nodes, or c) combinations thereof. A PBN may accommodate more than one predictor function 113. Thus, for every target node 115, there may correspond a set of predictor functions 113. In some embodiments, a predictor function 113 may incorporate binary, ternary, or other multivariate logic. In one embodiment, the predictor function incorporates binary logic. In other embodiments the predictor function may incorporate ternary logic. In yet other embodiments the predictor function may incorporate other multivariate logic. In still other embodiments predictor functions may incorporate one of a variety of logic combinations.

Also illustrated in FIG. 1 are predictor probabilities 114, which are the probabilities that an associated predictor will be used in the determination a target node 115. A more detailed discussion of predictor probability can be found herein. In a basic building block 110 of a network such as is illustrated in FIG. 1, a number of predictor functions 113 may share common input nodes 111 while their outputs are synthesized, in this case by random selection of a predictor function 113, into an output or target node 115. A wiring diagram for the entire PBN would consist of n such building blocks. Thus, a PBN G(V,F) may be defined by a set of nodes $V=\{x_1, \ldots, x_n\}$ and the list of predictors $F=(F_1, \ldots, F_n)$ with their associated predictor probabilities, PBNs are defined in more detail herein.

There are various reasons for utilizing a probabilistic network. One such reason is that a Boolean model incorporates only a partial description of a physical system. This means that a Boolean function giving the next state of a variable is likely to be only partially accurate. There will be occasions when different Boolean functions may actually describe the transition, but these are outside the scope of the conventional Boolean model. If, consequently, an uncertainty exist as to which transition rule should be used, then a PBN involving a set of possible Boolean functions for each variable may be more suitable than a network in which there is only a single function for each variable.

One embodiment of the invention constructs a PBN representing regulatory networks, such that the model class: (a) incorporates rule-based dependencies between nodes; (b) allows the systematic study of global network dynamics; (c) is able to cope with uncertainty, both in the data and the model selection; and (d) permits the quantification of the relative influence and sensitivity of nodes in their interactions with other nodes.

Certain embodiments include methods for searching a representative network having a plurality of nodes; listing a cumulative measure of association of a node with at least one other node; repeating the search process for each node of the network; listing a cumulative measure of association for each node of the network; saving the list of cumulative measure of association; selecting a predetermined number of node combinations in the system, (e.g., selecting the top 5 combinations with the highest cumulative measure(s) of association for at least one target node); constructing predictor functions for at least one of the combinations selected, and transforming the cumulative measure of association (e.g., coefficient of determination) associated with selected combination into a probability, a predictor probability.

Various complex systems may be represented by a network and analyzed using methods described herein, including, but not limited to gene regulatory systems, cell regulatory systems, physiologic systems, biological systems, ecosystem, and other complex systems, such as financial systems, sociologic systems, and the like. Network nodes may be representative of factors that may influence a system of interest. Nodes of a network for a biological system for example, may represent gene expression, protein-protein interactions, protein phosphorylation, protein levels, protein activity, protein modifications, carbohydrate levels, lipid levels, stress, radiation, and other conditions or measurements that may influence a biologic system. Biologic systems that may be analyzed include, but is not limited to eukaryotes, prokaryotes, viruses, bacteria, plants, animals, cultivated plants, mammals, humans, farm animals and the like. In one embodiment methods may be used to model a disease state to identify a therapeutic target or to diagnose a particular condition. In other embodiments the addition of a node(s) to a network may also be analyzed to determine an effect on a network as a result of the introduction of a new node(s), for example in analyzing an effect of additional influence on a biologic system, such as the physiology of a crop plant or farm animal, resulting from a) introduction of a transgene, b) alteration in growth environment, c) alteration in diet, d) exposure to hormones, small molecules, proteins, genes, lipids, carbohydrates and other substances that may affect the system in which they are introduced.

The maximum number of functions used to predict a target node (e.g., gene expression, protein activity, etc.) may be increased or decreased depending on the amount of training data available. For example, rather than a single Boolean function of four variables, which would make the model deterministic and limit the regulatory modeling of the target gene to four variables, one could use a PBN with two Boolean functions of three variables each. This would make the model non-deterministic and allow the effects of up to six variables on the target gene. The greater flexibility of the PBN, and therefore its ability to model richer systems by fitting richer data sets, can be balanced with increased design complexity relative to both the number of predictor functions per gene and the number of input nodes upon which those predictor functions operate. The PBN can be constructed so as to involve many simple but good predictors rather than one complex but poor one, thus, rather than fitting one overly complex model to the data, one can fit many simple models and use them in a concerted manner. In certain embodiments of the invention functions other than Boolean functions may be used as predictor functions.

Certain embodiments relate to systems and methods for analyzing complex systems and constructing PBNs for complex systems. In one embodiment, the system comprises a means for providing data for a plurality of nodes; a means for pre-processing (e.g., normalizing or transforming data) data for input; a means for searching and comparing data representative of nodes for each of a plurality of nodes; a means for assigning a cumulative measure of association to each node; a means for repeating searching, comparing, assigning a cumulative measure of association for at least one other network node; a means for selecting a plurality of input node combinations for synthesis of an output node; a means for constructing a set of predictor functions for each combination and/or sub-combinations of input nodes; a means for transforming a cumulative measure of association related to a combinations or sub-combinations of input nodes into a predictor probability; a means for constructing a PBN; and a means for transforming a result of a process for delivery to a user and/or end-user. More specifically, this system further comprises means for constructing PBNs.

In certain embodiments, methods described herein may be used to identify therapeutic targets, such as proteins, enzymes, genes, and other drug targets in a cell, organ, organism, or biologic system. A therapeutic target may be directly or indirectly effect the properties or state of another node(s) of the modeled biologic system. An exemplary therapeutic target identification method includes constructing a probabilistic network (e.g., a Probabilistic Boolean Network), having a plurality of nodes, representing a biological network; inputting a value for at least one node of the probabilistic network; evaluating the probabilistic network to identify at least one node of the biological network as a target for therapeutic intervention. In other embodiments methods may be used to identify a target for manipulation that affects the state of biological or other complex system that may include constructing a probabilistic network (e.g., a PBN), having at least one node representing a biological network or other complex system; receiving input values for at least one node in the probabilistic network; evaluating a state of the probabilistic network at a plurality of time points; and identifying a node of the biological network or other complex system for manipulation to achieve a desired state of the biologic network.

In yet other embodiments a method may be used to identify or diagnose a particular state of a biological system, such as cancer, autoimmune diseases, hormone imbalances, nutritional state and the like. Methods may include constructing a probabilistic network having at least one node, for a biological network; receiving input values for at least one node of the probabilistic network; and diagnosing or determining a state of a biological network by analysis of the probabilistic network.

FIG. 2 illustrates an exemplary embodiment of a method of the present invention. In the illustrated embodiment, values for a plurality of network nodes are first input or received (block 210). Next, a combination of network nodes associated with a state of at least one other network node is selected (block 212). Associations may then be identified by computing a cumulative measure of association, such as a coefficient of determination. A cumulative measure of association between the combination of network nodes and at least one other network node is then determined (block 214) and network node data may then be utilized in constructing a plurality of predictor functions for a value of at least one other network node given the combination of network nodes (block 216). Predictor probabilities are next determined by transforming the cumulative measure of association between the combination of network nodes and at least one other network node into a predictor function probability (block 218). Predictor functions and predictor probabilities may thereafter be used in constructing a network representative of a complex system utilizing the plurality of predictor functions and the predictor function probabilities (block 220). In certain embodiments the measure of association between nodes or groups of nodes may use CODs for the determination of predictor probability. The combinations of predictor functions, predictor probabilities, and a node(s) of interest are typically used to construct a plurality of PBN building blocks that may be associated and/or interconnected with a number of other building blocks to form a PBN.

A method of inference, based on the coefficient of determination typically produces a number of good candidate predictors for each node (e.g., target gene or target protein). Since the COD itself is estimated from the data, there is little reason to rely on one good predictor function. Thus, the general approach is to probabilistically synthesize good predictor functions such that each predictor function's contribution is proportional to its determinative potential. For small sample sizes, the complexity of each predictor function can be limited. As new data make themselves available, the model class naturally allows one to narrow down as needed, effectively reducing the uncertainty for predicting each node (e.g., target gene).

Inference algorithms may be applied to a set of data (e.g., gene expression, protein interaction data, etc.). Because of the limited number of samples and the relative simplicity of the potential predictor functions, in one embodiment a full search for each optimal predictor is performed, rather than relying on a heuristic, sub-optimal solution the error of which cannot be reliably estimated. Consequently, the combinatorial nature of the search space and the relative simplicity of individual predictors is naturally well suited for distributed computing. For example, for any three genes, there are only 256 Boolean functions to search through to obtain the optimal estimate while there are many three-gene combinations. Implementation of such a prediction algorithm on a massively parallel supercomputer has been described.

In addition to the advantages mentioned above, a framework of PBNs may retain the appealing properties of Boolean networks, such as rule-based dependencies between nodes as well as the amenability to global analysis of dynamics. The rich and mature theory of Markov chains provides many useful tools for the latter. Another advantage of PBNs is that they naturally allow one to incorporate prior knowledge, if necessary. Thus, if certain regulatory relationships are known to exist, the class of the functions for the nodes in question can be constrained such that they reflect this prior knowledge. For instance, if it is known that for a certain collection of genes, the activation of genes cannot cause inhibitory effects on the target gene, then we can restrict our attention to the class of monotone Boolean functions, effectively reducing the search space. As another example, if it is believed that for certain classes of genes, canalizing functions (functions that have at least one input that can by itself determine the activity of the regulated element) provide the proper class of rules, then this constraint can be easily introduced into the inference algorithm.

In various embodiments, methods for constructing a network representative of a complex system includes (a) receiving values for a plurality of network nodes; (b) selecting a combination of network nodes associated with a state of at least one other network node; (c) determining a cumulative measure of association between the combination of network nodes and at least one other network node; (d) constructing a plurality of predictor functions for a value of at least one other network node given the combination of network nodes; (e) transforming the cumulative measure of association between the combination of network nodes and at least one other network node into a predictor function probability; and (f) constructing a network representative of a complex system utilizing the plurality of predictor functions and the predictor function probabilities. In certain embodiments, the network is representative of a biological system, in particular a gene regulatory network.

In other embodiments, methods for constructing a gene network representative of a complex gene regulatory system comprise (a) receiving values for a plurality of gene network nodes; (b) selecting a combination of gene network nodes associated with a state of at least one other gene network node; (c) determining a cumulative measure of association between the combination of gene network nodes and at least one other gene network node; (d) constructing a plurality of predictor functions for a value of at least one other gene network node given the combination of network nodes; (e) transforming the cumulative measure of association between the combination of gene network nodes and at least one other gene network node into a predictor function probability; and (f) constructing a network representative of a complex system utilizing the plurality of predictor functions and the predictor function probabilities.

In some embodiments, an apparatus may comprise a machine readable medium containing instructions which, when executed by a machine, cause the machine to perform operations comprising (a) receiving values for a plurality of network nodes; (b) selecting a combination of network nodes associated with a state of at least one other network node; (c) determining a cumulative measure of association between the combination of network nodes and at least one other network node; (d) constructing a plurality of predictor functions for a value of at least one other network node given the combination of network nodes; (e) transforming the cumulative measure of association between the combination of network nodes and at least one other network node into a predictor function probability; and (f) constructing a network representative of a complex system utilizing the plurality predictor functions and the predictor function probabilities.

In various embodiments, a method can comprise (a) identifying a plurality of network nodes related to a state of at least one other network node within a network, wherein each network node of the network includes a network node value which influences a gene expression state; (b) constructing a plurality of predictor functions from a combination of network nodes utilizing at least one of the network node values for at least one target node; (c) determining a cumulative measure of association for combinations of network nodes; (d) transforming the cumulative measure of association into a probability that any one of a plurality of predictor functions is utilized to determine a state of at least one other node of a network; and (e) connecting a plurality of network node combinations to construct a probabilistic Boolean network.

In some embodiments, methods may include therapeutic target identification comprising (a) constructing a Probabilistic Boolean Network, having a plurality of nodes, wherein the PBN is representative of a gene network; (b) inputting a value for at least one node of the Probabilistic Boolean Network; and (c) evaluating the Probabilistic Boolean Network to identify at least one node of the Probabilistic Boolean Network as a target for therapeutic intervention.

In other embodiments, a method comprising (a) constructing a probabilistic Boolean network, having at least one node, for a biologic network; (b) inputting a value for at least one node in the probabilistic Boolean network; (c) evaluating a state of the probabilistic Boolean network at a plurality of time points; and (d) identifying a node of the biologic network for manipulation to achieve a desired state of the biologic network is contemplated.

In certain embodiments, a diagnostic method comprising (a) constructing a probabilistic network having at least one node, for a biological network; (b) inputting values for at least one node of the probabilistic network; and (c) diagnosing a particular state of the biological network by analysis of the probabilistic network is contemplated.

In operation, the means for receiving network node data, the means for normalizing or transforming network node data, the means for searching data representative of network nodes for associations between nodes, the means for listing the cumulative measures of association between nodes, the means for saving the listings, the means for selecting a number of node combinations based on the cumulative measure of association, the means for constructing a set of predictors for each combination of nodes selected, the means for transforming a measure of association into a predictor probability, the means for constructing a PBN that establishes the regulatory relationship between network nodes and the means for transforming the output of a PBN for end-user use may involve a programmed computer with the respective functionalities described herein, implemented in hardware, software, and/or firmware, or a combination thereof; a logic circuit or other component of a programmed computer that performs the operations specifically identified herein, dictated by a computer program; or a computer memory encoded with computer-executable instructions representing a computer program that can cause a computer to perform functions, processes, and/or methods described herein.

FIG. 3 illustrates an example of a general-purpose computer system that may be used to provide and/or execute the methods, systems, and software embodiments of the present invention. FIG. 3 shows a computer system 300 comprising a monitor 310 having a screen 320, a system unit 330, a keyboard 340, and a mouse 350. System unit 330 may house other computer components (e.g., a processor, a memory, etc. further described herein). Various embodiments of the present invention include memories, processing elements, Application Specific Integrated Circuits (ASICs), and/or programmable logic devices (PLDs). Such memories may comprise a machine-readable medium on which may be stored a set of instructions (i.e., software) embodying any one, or all, of the functions, processes, or methods described herein. Such instructions may reside, completely or partially, within an illustrated memory as well as within alternative machine-readable media such as a processing element, ASIC, PLD, or mass-storage device further described herein.

FIG. 4 and the following discussion is intended to provide a brief, general description of a suitable computing environment for the computer programs described above. The method for analyzing biologic systems by applying a probabilistic network is typically implemented in computer-executable instructions organized in program modules. Program modules may include various routines, programs, objects, components, and/or data structures utilized to perform the functions, processes, and methods and implement the data types described herein.

FIG. 4 illustrates an exemplary block diagram including a computer system suitable for execution of the system software embodiments of the invention (e.g., computer system 300 of FIG. 3). In certain embodiments the method, system, and software embodiments of the present invention may be implemented in other data processing systems, including multiprocessor systems, microprocessor-based and/or programmable consumer electronics, minicomputers, mainframe computers, and the like. The invention may also be used in distributed computing environments where tasks are performed utilizing remote data processing systems or devices that are linked via a communications network. In a distributed computing environment, program modules may be located in both local and remote machine or computer-readable media.

The system shown in FIG. 4 includes a server computer system 420, including a processing unit 421 (e.g., one or more processing devices), a system memory 422, and a system bus 423 which interconnects various system components including system memory 422 to processing unit 421. The system bus 423 may comprise any of several types of bus structures including a memory bus, a memory controller, a hub, a local bus implementing a bus architecture such as peripheral component interconnect (PCI), Video Electronics Standards Association (VESA), or Microchannel (MCA), and/or a peripheral or input/output (I/O) bus, e.g., an Industry Standard Architecture (ISA), Extended Industry Standard Architecture (EISA), Universal Serial (USB), or IEEE 1394 "Firewire" bus.

System memory 422 may include read only memory (ROM) 424 and/or random access memory (RAM) 425 as illustrated. A basic input/output system 426 (BIOS), containing the basic routines that help to transfer information between components within server computer system 420, such as during start-up, is stored in ROM 424. Server computer system 420 further may include one or more mass storage devices such as a hard disk drive 427, a floppy disk drive 428, e.g., to read from or write to a removable "floppy" disk 429, and/or an optical disk drive 430, e.g., for reading from or writing to a CD-ROM disk 431 or other optical media. Hard disk drive 427, floppy disk drive 428, and optical disk drive 430 may be connected to the system bus 423 by a hard disk drive interface 432, a floppy disk drive interface 433, and an optical disk drive interface 434, respectively. The drives and their associated computer-readable media provide nonvolatile storage of data, data structures, computer-executable instructions (program code such as dynamic link libraries, and executable files), etc. for server computer system 420. Although the description of computer-readable media above refers to a hard disk, a removable magnetic disk and a CD, it may also include other types of media that are readable by a computer, such as magnetic cassettes, flash memory, digital video disks, Bernoulli cartridges, and the like.

A number of program modules may be stored in mass storage devices, e.g., 427, 428, and 430, and system memory 422 including an operating system 435, one or more application programs 436, other program modules 437, and program data 438. A user may enter commands and information into the personal computer 420 through a keyboard 440 and pointing device, such as a mouse 442. Other input devices (not shown) may include a trackball, graphics tablet, light pen, microphone, joystick, game pad, satellite dish, scanner, or the like. These and other input devices may often be connected to the processing unit 421 through a serial port interface 446 that is coupled to the system bus 423, but may be connected via other interfaces, such as a parallel port interface, game port interface, a USB controller, or the like. A monitor 447 or other type of display device is also connected to the system bus 423 via an interface, such as a display controller or video adapter 448. In addition to monitor 447, a computer system may further include other peripheral output devices (not shown), such as speakers and printers.

In one embodiment, server computer system 420 may operate in a networked environment via connections to one or more remote computers, such as client computer system 449. In alternative embodiments of the present invention a remote computer may comprise a server computer system, a router, a gateway, a hub, a peer device, or other common network node, typically including many or all of the elements described relative to the server computer system 420. Connections depicted in FIG. 4 include a local area network (LAN) 451 and a wide area network (WAN) 452. Such networking environments are commonplace in offices, enterprise-wide computer networks, extranets, intranets, and the Internet/World Wide Web (WWW).

When used in a LAN networking environment, server computer system 420 is depicted in the illustrated embodiment as being connected to local network 451 through a network interface or adapter 453. When used in a WAN networking environment, server computer system 420 may include a modem 454 or other conventional means for establishing communications over the wide area network 452 (e.g., the Internet). The modem 454, which may be internal or external, may be connect to the system bus 423 via the serial port interface 446 as shown or via a variety of other components utilizing well-known techniques. In a networked environment, program modules depicted relative to server computer system 420, or portions thereof, may be stored in the remote memory storage device, e.g., a memory storage device within client computer system 449 (not shown). The network connections shown are merely examples and other means of establishing a communications link between the computers may be used.

Although described in the context of computer systems 300, 420, and 449, the present invention may be implemented in any suitable data processing system having a greater or lesser number of system components. For example, client computer system 449 of FIG. 4 may, in alternative embodiments of the invention, comprise a workstation, personal computer, "thin client" (i.e. network computer or NetPC), Internet appliance, terminal, palmtop computing device, robust cellular or Personal Communications Services (PCS) telephone, or the like. Similarly, server computer system 420 of FIG. 4 may comprise a wide variety of data processing systems. For example, in alternative embodiments of the present invention server computer system 420 may comprise a personal computer system, a dedicated or "thin server", a mainframe, a super computer, a parallel computer, or the like.

In certain embodiments, one or more protocols from the Internet Suite of protocols are used so a communications network includes an intranet, internet or the like. Such a communications network may communicate with other public or private networks using protocols from the Internet Suite. As is known in the art, the Internet Suite of protocols includes such protocols as the Internet Protocol ("IP"), Transmission Control Protocol ("TCP"), User Datagram Protocol ("UDP"), Hypertext Transfer Protocol ("HTTP"), Hypertext Markup Language ("HTML"), extensible Markup Language ("XML") and others.

One or more private databases, and one or more public databases may be multi-user, multi-view databases that store experimental data as well as results of the methods described. The databases may use relational database, object-oriented database, or object-relational database tools and structures. The data stored within the one or more internal proprietary databases may not be available to the public. Databases are typically made available to the public through a publicly accessible database server using selected security features (e.g., login, password, encryption, firewall, etc.). A public database(s) may include experimental data and other information in the public domain and are also multi-user, multi-view databases. A public database(s) include such well known public databases such as those provided by Medline, GenBank, SwissProt, and other known public databases.

Within the present description the terms "computer-readable medium/media" and/or "machine-readable medium/media" shall be taken to include any mechanism that provides (i.e., stores and/or transmits) information in a form readable by a machine (e.g., a computer). For example, a machine-readable medium includes read only memory (ROM); random access memory (RAM); magnetic disk storage media; optical storage media; flash memory devices; electrical, optical, acoustical or other form of propagated signals (e.g., carrier waves, infrared signals, digital signals, etc.); etc. While specific illustrative embodiments are described the invention may be implemented with any known data processing and communication network and are not limited to any specific architecture or configuration.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The term "plurality" refers to two or more.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
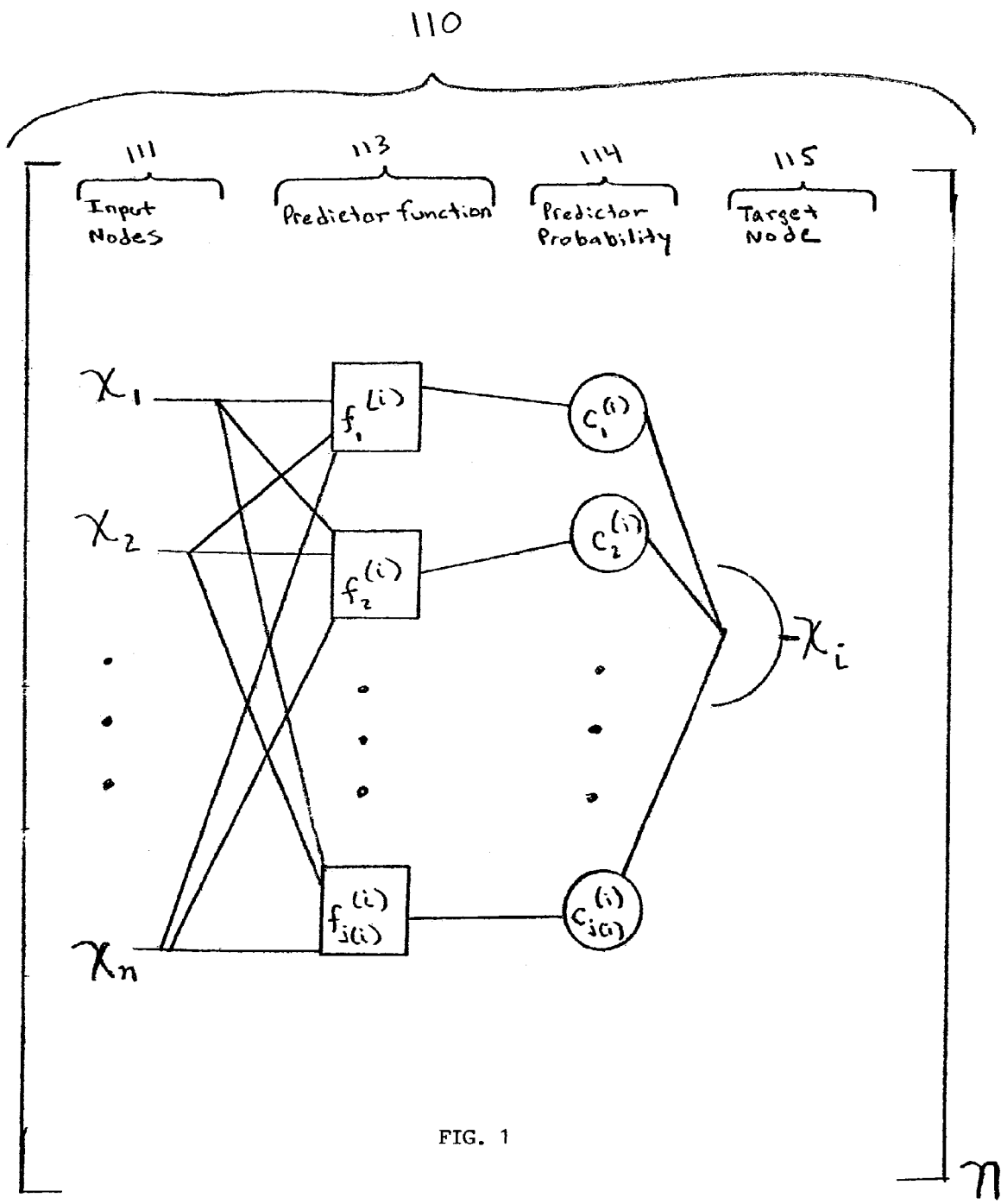
FIG. 1 illustrates an exemplary building block of a PBN.
Figure 2:
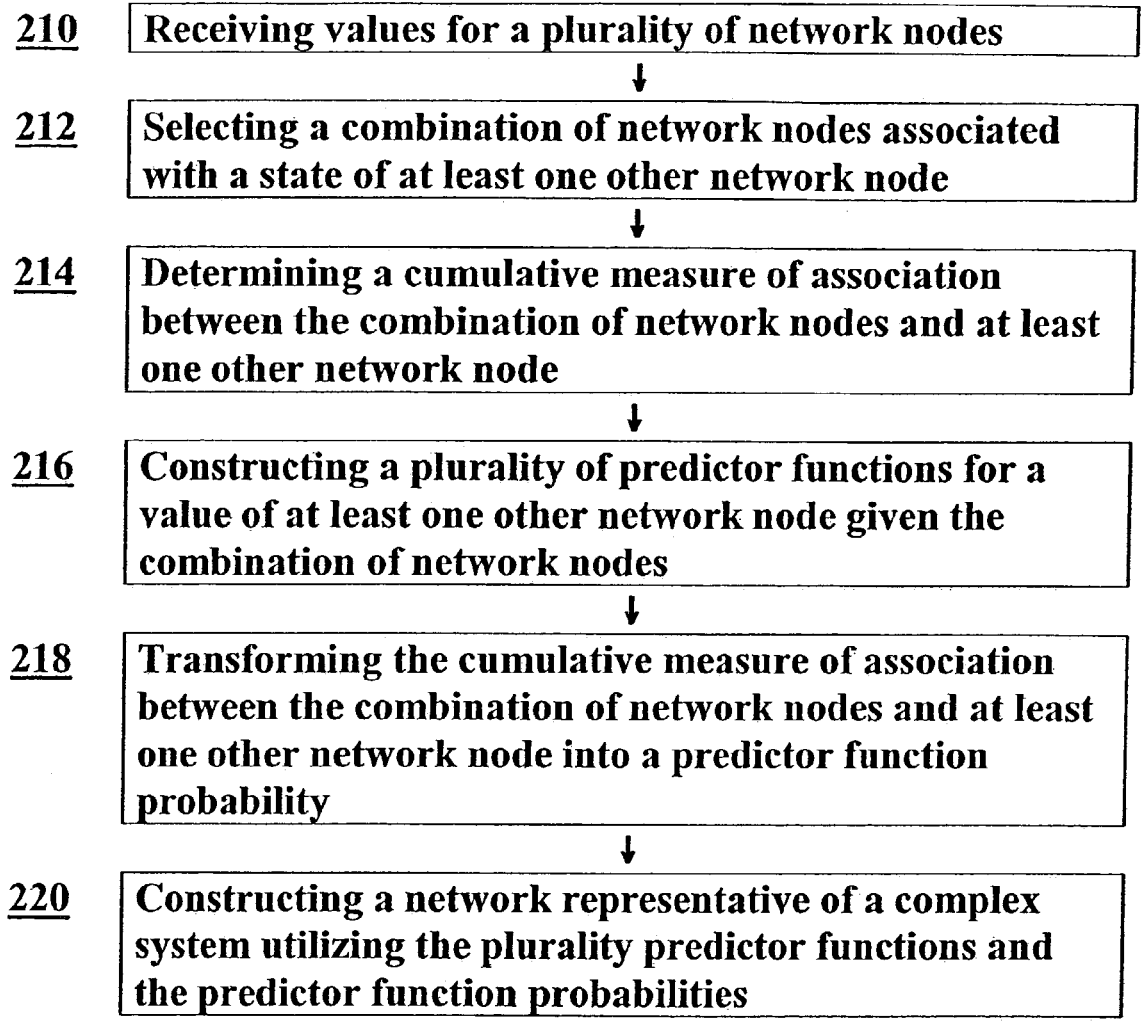
FIG. 2 illustrates an exemplary embodiment of methods.
Figure 3:
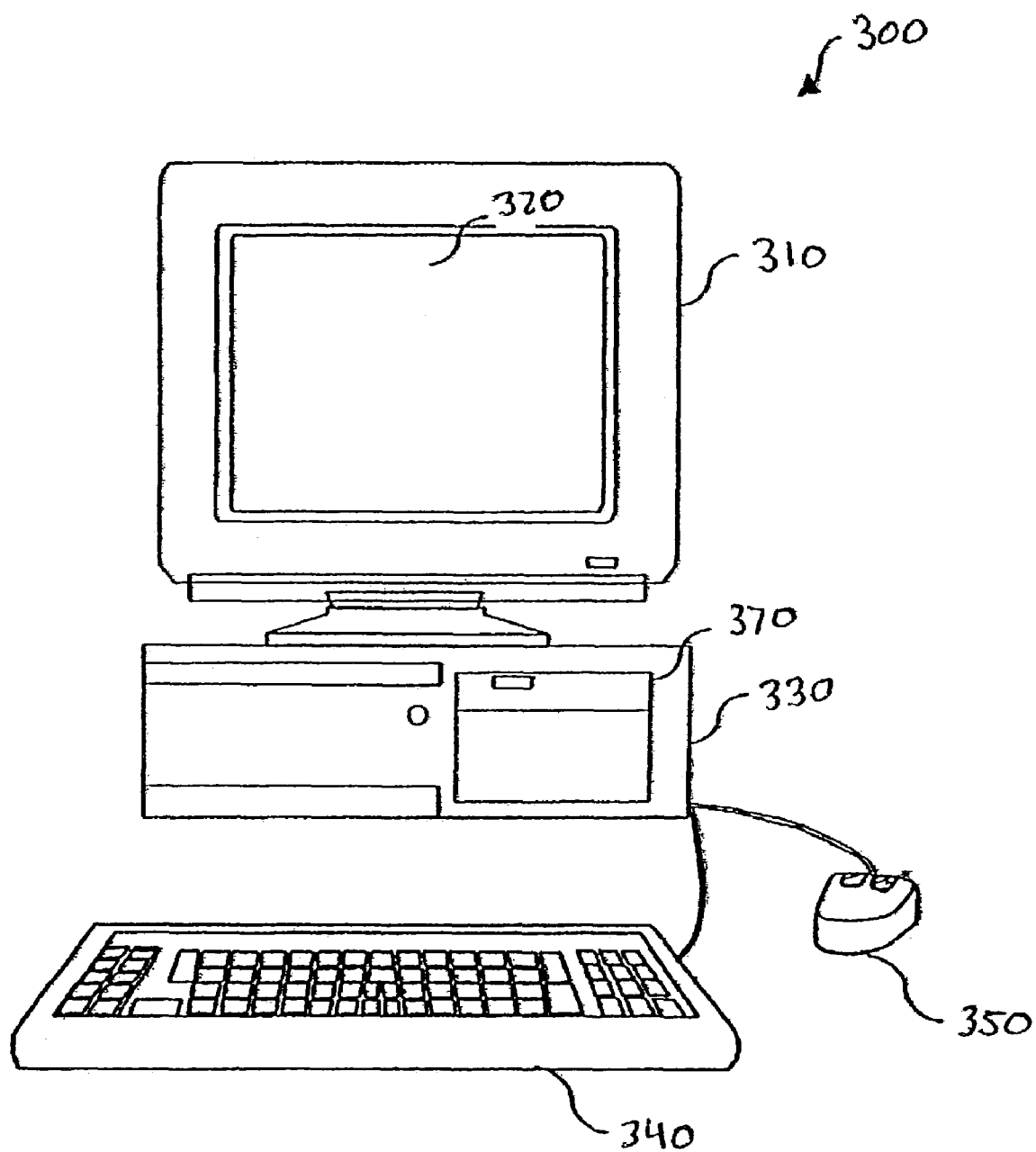
FIG. 3 illustrates an example of a computer system that may be used to execute the methods and software embodiments of the present invention.
Figure 4:
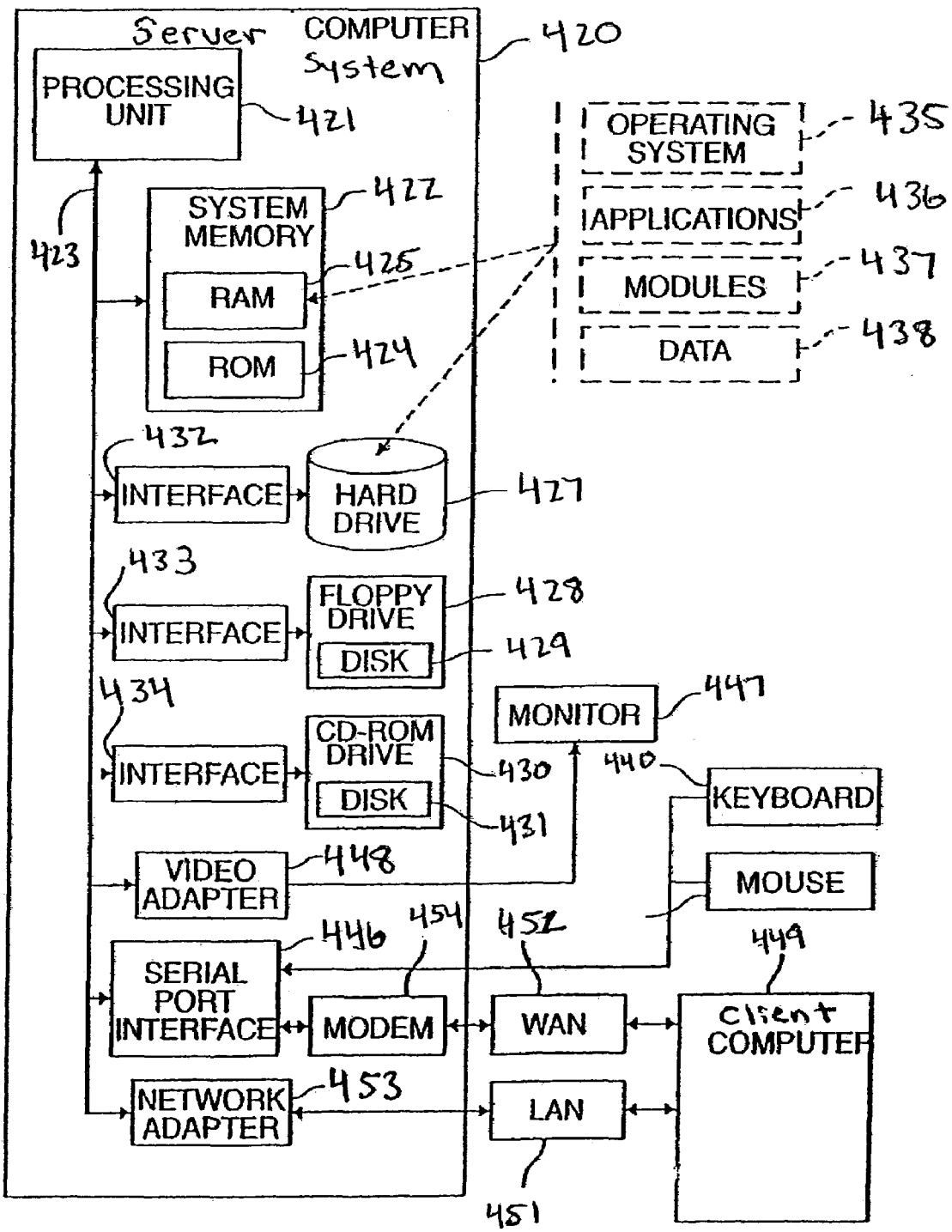
FIG. 4 illustrates an exemplary block diagram of a computer system suitable for execution of the system software embodiments of the invention.

Limitations of standard Boolean networks include an inherent determinism. From a conceptual point of view, it is likely that the regularity of genetic function and interaction known to exist is not due to hard-wired logical rules, but rather to the intrinsic self-organizing stability of the dynamical system, despite the existence of stochastic components in the cell. Empirically, the assumption of only one logical rule per gene may lead to incorrect conclusions when inferring these rules from gene expression measurements, as the latter are typically noisy and the number of samples is small relative to the number of parameters to be inferred. Various embodiments of the invention describe Probabilistic Boolean Networks (PBNs), an improved model and method for constructing and analyzing a network representative of a complex system.

The inventors assert that genetic regulatory networks function in what might be called a multiscale manner. While multiscale modeling has been fundamental in the development of many fields, such as computing, material science, and image processing (Melnik et al., 2001; Dougherty et al., 2001), its use in genetic network analysis could prove to be invaluable. One of the basic principles in multiscale modeling is that meaningful and useful information about a system or object exists on several different "levels" simultaneously. In the context of genetic networks, this would imply that genes form small groups (or clusters) within each of which genes have close interactions; then, some of these clusters form larger "meta-clusters" and these meta-clusters have interactions as well. This process may continue on several different "scales." This type of clustering effect has been observed in many other types of networks, such as social networks (Newman et al., 2002), the power grid of the western United States, and neural networks (Watts and Strogatz, 1998). Interestingly, dynamical systems that have this property exhibit enhanced signal-propagation speed and computational power.

One of the various embodiments of the invention includes methods to identify relatively small sub-networks, out of a large network, that function more or less independently of the rest of the network. Such a small sub-network would require little or sometimes even no information from the "outside." The inventors will proceed by starting with a "seed" consisting of one or more genes that are believed to participate in such a sub-network. Then, iteratively adjoin new genes to this sub-network such that the "autonomy" of the sub-network is maintained as much as possible. An example of such a sub-network, generated using glioma gene-expression data produced in the inventors laboratory, is described in Example 6 below. Work in this direction has focused on the theoretical framework for performing such operations as adjoining new genes such that the network structure and parameters remain consistent with the data.

The procedure for iteratively "growing" sub-networks from seeds will make use of the influences and sensitivities of genes. Informally speaking, the basic idea is to iteratively adjoin new genes to the sub-network such that they are least sensitive to the influences of other genes outside the existing sub-network, but at the same time, have significant interactions with the genes inside the sub-network, where such interactions are measured by the influences and sensitivities.

Finally, development of good visualization tools for working with influences and sub-networks is contemplated. The Inventors envision graphical user interfaces that allow the user to interactively choose genes from a large list of genes and display the potential interactions, in terms of influences and sensitivities, on an already displayed sub-network. Such a tool will allow the user to visually compare the sub-network models with other existing models and known pathway interactions. Some visualization tools have already been developed for the multivariate gene prediction based on the coefficient of determination (Suh et al., 2002). These existing visualization tools, in light of the present disclosure may be adapted for use with the inventive methods.

I. Probabilistic Boolean Networks (PBN)

Even if one is fairly confident that a model is sufficiently robust that other variables can be ignored without significant impact, there remains the problem of inferring the functions (e.g., Boolean functions, etc.) from sample data. In the case of gene expression microarrays, the data may be severely limited relative to the number of variables in the system. Should it happen that a particular Boolean function has even a moderately large number of essential variables, then its design from the data is likely to be imprecise because the number of possible input states will be too large for precise estimation. This situation may be exacerbated if some essential variables are either unknown or unobservable. As a consequence of the inability to observe sufficient examples to design the transition rule, it may be necessary to restrict the number of variables over which a function is defined. For each subset of the full set of essential variables, there may be an optimal function, in the sense that the prediction error is minimized for that function, given the variables in the subset. These optimal functions must be designed from sample data. Owing to inherent imprecision in the design process, it may be prudent to allow a random selection between several functions, with the weight of selection based on a probabilistic measure of worth, such as the coefficient of determination (COD). The COD, as discussed below, measures the degree to which an observed node value can be used to improve the prediction of a target node relative to the best possible prediction in the absence of the observations.

In certain embodiments, an open system may be modeled, rather than a closed system. Depending upon a particular external condition at a given moment of time, the system may transition differently than it would in the absence of that condition. Such effects have been considered in the framework of using the coefficient of determination in the presence of external stresses. Under the assumption that the external stimuli occur asynchronously, it is prudent to allow uncertainty among the transition rules and weight their likelihood accordingly. It may be that the probability of applying a Boolean function corresponding to an unlikely condition is low; however, system behavior might be seriously misunderstood if the possibility of such a transition is ignored.

Given several good competing functions for a given node, there is little reason to rely on only one of them. The deterministic rigidity of Boolean networks may be overcome by extending the Boolean network concept to a probabilistic setting, as in Probabilistic Boolean Networks (PBNs). A PBN may accommodate more than one possible function (predictor) for each node. Thus, to every node ($x_i$), there corresponds a set of predictors ($F_i$)

$$F_i = \{f_j^{(i)}\}_{j=1,...,l(i)} \quad (1)$$

where each $f_j^{(i)}$ is a possible function determining the value of node $x_i$ and $l(i)$ is the number of possible functions for node $x_i$. The functions $f_j^{(i)}$ may be called predictors, since the process of inferring these functions from measurements or equivalently, of producing a minimum-error estimate of the value of a node at the next time point, is known as prediction in estimation theory. A realization of a PBN at a given instant of time may be determined by a vector of Boolean functions. If there are N possible realizations, then there are N vector functions, $f_1, f_2, \ldots, f_N$ of the form $f_k = (f_{k1}^{(1)}, f_{k2}^{(2)}, \ldots, f_{kn}^{(n)})$, for $k=1,2, \ldots, N$; $1 \leq k_i \leq l(i)$ and where $f_{ki}^{(i)} \in F_i (i=1, \ldots, n)$. In other words, the vector function $f_k: \{0,1\}^n \to \{0,1\}^n$ acts as a transition function (mapping) representing a possible realization of the entire PBN. Thus, given the values of all nodes $(x_1, \ldots, x_n)$, $f_k(x_1, \ldots, x_n) = (x'_1, \ldots, x'_n)$ gives us the state of the nodes after one step of the network given by the realization $f_k$.

Now, let $f = (f^{(1)}, \ldots, f^{(n)})$ be a random vector taking values in $F_1 \times \ldots \times F_n$. That is, f can take on all possible realizations of the PBN. Then, the probability that predictor $f_j^{(i)}$ is used to predict node $i (1 \leq j \leq l(i))$ is equal to $$c_j^{(i)} = Pr\{f^{(i)} = f_j^{(i)}\} = \sum_{k: f_{ki}^{(i)} = f_j^{(i)}} Pr\{f = f_k\} \quad (2)$$

Since the predictor probability or $c_j^{(i)}$ are probabilities, they must satisfy $$\sum_{i=1}^{l(i)} c_j^{(i)} = 1 \quad (3)$$

It is not necessary that the selection of the predictors composing a specific network be independent. This means that it is not necessarily the case that $Pr\{f(i)=f_j^{(i)}, f^{(l)}=f_k^{(l)}\} = Pr\{f^{(i)}=f_j^{(i)}\} \cdot Pr\{f^{(l)}=f_k^{(l)}\}$.

A PBN is said to be independent if the random variables $f^{(1)}, f^{(2)}, \ldots, f^{(n)}$ are independent. In the dependent case, product expansions such as the one given in the preceding equation, as well as ones involving more functions, require conditional probabilities. Henceforth, unless otherwise mentioned, independent PBNs will be assumed.

A PBN G(V,F) may be defined by a set of nodes $V=\{x_1, \ldots, x_n\}$ and the list $F=(F_1, \ldots, F_n)$, where the latter is defined in equation (1). Assuming independence, $$N = \prod_{i=1}^{n} l(i)$$

is the number of possible PBN realizations. If $l(i)=1$ for all $i=1, \ldots, n$, then $N=1$ and the PBN reduces to a standard Boolean network.

The dynamics of the PBN are similar to the dynamics of Boolean networks, but at any given point in time, the value of each node is determined by one of the possible predictors (predictor functions), chosen according to its corresponding probability (predictor probability). This can be interpreted by saying that at any point in time, we have one out of N possible networks. To calculate the probability that a particular network is selected. Let us define the matrix $$K = \begin{bmatrix} 1 & 1 & \cdots & 1 & 1 \\ 1 & 1 & \cdots & 1 & 2 \\ \cdots & \cdots & \cdots & \cdots & \cdots \\ 1 & 1 & \cdots & 1 & l(n) \\ 1 & 1 & \cdots & 2 & 1 \\ 1 & 1 & \cdots & 2 & 2 \\ \cdots & \cdots & \cdots & \cdots & \cdots \\ 1 & 1 & \cdots & 2 & l(n) \\ \cdots & \cdots & \cdots & \cdots & \cdots \\ l(1) & l(2) & \cdots & l(n-1) & l(n) \end{bmatrix}$$

containing lexicographically ordered rows, each one corresponding to a possible network configuration. That is, row m corresponds to network m and the entry j in the ith column specifies that predictor $f_j^{(i)}$ should be used for gene $x_i$. K is an N×n matrix. Using this matrix, the probability that network i is selected may be represented by $$Pi = Pr\{\text{Network } i \text{ is selected}\} = \prod_{j=1}^{n} c_{K_{ij}}^{(j)}, \quad (4)$$

where $K_{ij}$ is the ijth entry in matrix K. It may be checked that $$\sum_{i=1}^{N} P_i = 1$$

by noting that $$\sum_{i=1}^{N} P_i = \sum_{i=1}^{N} \prod_{j=1}^{n} c_{K_{ij}}^{(j)} = \prod_{j=1}^{n} \sum_{i=1}^{l(j)} c_i^{(j)} = \prod_{j=1}^{n} 1 = 1 \quad (5)$$

where we have used equation (3).

Now, consider the state space of the PBN, also consisting of $2^n$ states. Similarly to the discussion of the dynamics of Boolean networks below, the interest is in establishing the state transition matrix A. In this case, however, the network may transition from a state to a number of other possible states, hence defining a random process. The probability of transitioning from state $(x_1, \ldots, x_n)$ to state $(x'_1, \ldots, x'_n)$ can be obtained as $$Pr\{(x_1, \ldots, x_n) \to (x'_1, \ldots, x'_n)\} = \quad (6)$$

$$\sum_{i: f_{K_{i1}}^{(1)}(x_1,\ldots,x_n)=x'_1, f_{K_{i2}}^{(2)}(x_1,\ldots,x_n)=x'_2,\ldots,f_{K_{in}}^{(n)}(x_1,\ldots,x_n)=x'_n} P_i$$

$$= \sum_{i=1}^{N} P_i \underbrace{\left[\prod_{j=1}^{n} \left(1 - |f_{K_{ij}}^{(j)}(x_1, \ldots, x_n) - x'_j|\right)\right]}_{\in \{0,1\}}$$

where in the last expression, binary values are treated as real values. Since $P_i = Pr\{\text{Network } i \text{ is selected}\}$, equation (6) can be interpreted as $$Pr\{(x_1, \ldots, x_n) \to (x'_1, \ldots, x'_n)\} = \sum_{i=1}^{N} Pr\{(x_1, \ldots, x_n) \to (x'_1, \ldots, x'_n)|\text{Network } i \text{ selected}\} \cdot P_i$$

and $Pr\{(x_1, \ldots, X_n) \to (x'_1, \ldots, x'_n)|\text{Network } i \text{ is selected}\} \in \{0,1\}$, as is the case for standard Boolean networks, described below. By using equations (5) and (6), and the fact that for any $(x_1, \ldots, x_n)$ there always exists an $(x'_1, \ldots, x'_n)$ and $i$ such that $$\prod_{j=1}^{n}\left(1 - |f_{K_{ij}}^{(j)}(x_1,\ldots,x_n) - x'_j|\right) = 1 \text{ we have that for any } i = 1, \ldots, 2^n. \text{ Thus, } A\sum_{j=1}^{2^n} A_{ij} = 1 \text{ is}$$

also a Markov matrix and the PBN is a homogeneous Markov process, meaning that the transition probabilities do not change with time. It also follows that A has at most $N \cdot 2^n$ non-zero entries and reduces to the binary state-transition matrix when N=1, as described below (see Example 1 below).

Inference of Predictors in Probabilistic Boolean Networks

In certain embodiments a set of predictors may be selected for a given node (e.g., gene, etc.) by employing a Coefficient Of Determination (COD). The COD measures the degree to which the levels of an observed node set (e.g., transcriptional levels of a gene set) can be used to improve the prediction of the level of a target node (e.g., gene transcription) relative to the best possible prediction in the absence of observations. For example, the node is a gene. Let $X_i$ be the target gene; $X_1^{(i)}, X_2^{(i)}, \ldots, X_{l(i)}^{(i)}$ be sets of genes: and $f_1^{(i)}, f_2^{(i)}, \ldots, f_{l(i)}^{(i)}$ be function rules such that $f_1^{(i)}(X_1^{(i)}), \ldots, f_{l(i)}^{(i)}(X_{l(i)}^{(i)})$ are optimal predictors of $X_i$ relative to some probabilistic error measure $\epsilon(X_i, f_k^{(i)}, (X_k^{(i)}))$, keeping in mind that $X_i$ and $f_k^{(i)}(X_k^{(i)})$ are random variables, for which we use upper case letters. For each k, the COD for $X_i$ relative to the conditioning set $X_k^{(i)}$ is defined by $$\theta_k^i = \frac{\varepsilon_i - \varepsilon(X_i, f_k^{(i)}(X_k^{(i)}))}{\varepsilon_i},$$

where $\epsilon_i$ is the error of the best (constant) estimate of $X_i$ in the absence of any conditional variables. The COD is between 0 and 1 and measures the relative decrease in error from estimating $X_i$ via $f_k^{(i)}(X_k^{(i)})$ rather than by just the best constant estimate. For instance, in the case of minimum mean-square error estimation, $\epsilon_i$ is the error of the mean of $X_i$, which is the best constant estimate, and $f_k^{(i)}(X_k^{(i)})$ is the conditional expectation of $X_i$ given $f_k^{(i)}(X_k^{(i)})$ that is, $f_k^{(i)}(X_k^{(i)}) = E\lfloor X_i|X_k^{(i)}\rfloor$. In practice, the COD must be estimated from training data with designed approximations being used in place of $f_1^{(i)}, f_2^{(i)}, \ldots, f_{l(i)}^{(i)}$. Consequently, the complexity of the functions $f_1^{(i)}, f_2^{(i)}, \ldots, f_{l(i)}^{(i)}$ and the amount of training data become an issue. For some microarray-based analysis, the number of genes in each predictor was kept to a maximum of three. The framework afforded by the PBN may be well suited for dealing with design imprecision due to limited sample size, where the domain of each predictor may need to be constrained due to lack of training data, but several predictors, with possibly different domains, may be collectively, employed.

Let us now assume that a class of gene sets $X_1^{(i)}, X_2^{(i)}, \ldots, X_{l(i)}^{(i)}$ possessing high CODs has been selected.

The designed approximations of the optimal function rules $f_1^{(i)}, f_2^{(i)}, \ldots, f_{l(i)}^{(i)}$ as the rule set for gene $X_i$ with the probability of $f_j^{(i)}$ being chosen (see equation (2)) given by $$c_k^{(i)} = \frac{\theta_k^{(i)}}{\sum_{j=1}^{l(i)} \theta_j^{(i)}},$$

where the CODs are the estimates formed from the training data. According to the above expression, those functions corresponding to the highest CODs will be selected more often in the probabilistic network. The number of chosen predictors, l(i), can be a user-selectable parameter and determines the amount of uncertainty that the model can handle.

Dynamics of Probabilistic Boolean Networks

The dynamic behavior of PBNs can be represented as a Markov chain where the state transition matrix A is completely specified by all of the possible Boolean functions and their probabilities. As such, the theory of the limiting behavior of Markov chains is directly applicable to the study of the dynamics of PBNs. For instance, suppose that in Example 1 below, the predictor probabilities are given by $c_1^{(1)}=0.6$, $c_2^{(1)}=0.4$, $c_1^{(2)}=1$, $c_1^{(3)}=0.5$, $c_2^{(3)}=0.5$, as shown in the bottom row of the network truth table. Then, the probabilities of the four networks can be computed via equation (4). For example, to compute $P_2$, we use row 2 of matrix K and get $P_2=c_1^{(1)}c_1^{(2)}c_2^{(3)}=0.6\times1\times0.5=0.3$. Thus, the probabilities of the four networks are: $P_1=0.3$, $P_2=0.3$, $P_3=0.2$, and $P_4=0.2$. Substituting those values into the matrix A and iterating equation 19, see below, supposing that the starting joint distribution of all the genes is uniform, that is, $$c_k^{(i)} = \frac{\theta_k^{(i)}}{\sum_{j=1}^{l(i)} \theta_j^{(i)}},$$

we find that the limiting probabilities are $\pi=[0.15, 0, 0, 0, 0, 0, 0, 0.85]$.

This indicates that in the long run, all three genes will either be OFF (000), with probability 0.15, or all three genes will be ON (111), with probability 0.85. These two states are called absorbing. This can be seen by looking at a state transition diagram corresponding to matrix A, shown in FIG. 5. Once the process moves into states (000) or (111), it never exits them. This notion corresponds to the concept of attractors in Boolean networks. Similarly, the concept of limit cycle attractors corresponds to the irreducible sets of states in the Markov chain, or in other words, those sets of states such that no state outside them can be reached from any state in them. One can think of the network as being trapped in those sets of states. Finally, the transient states in the Markov chain that lead to either absorbing states or irreducible sets of states correspond to the basins of attraction in Boolean networks. Thus, PBNs qualitatively exhibit the same dynamical properties as Boolean networks, but are inherently probabilistic and thus can cope with uncertainty.

An important consideration for PBNs, which is not an issue in Boolean networks, is whether or not there exists a steady-state distribution. For instance, in the above example, the probabilities of ending up in states (000) or (111) would be different if the starting distribution $D^0$ was also different. To illustrate this, suppose the starting distribution is $D^0=[1, 0, 0, 0, 0, 0, 0, 0]$, that is, the network begins in state (000) with probability 1. Then, it is clear that it will never escape that state and the limiting probabilities would also be $\pi=D^0$. Therefore, the question about where the PBN will end up in the long run can not be asked without specifying where it started.

Steady-State Distributions of PBNs

When considering the long-run behavior of a Markov chain, it is useful to consider equivalence classes within the set of states. This is especially true for genomic systems in which the state space can be extremely large, and it may be partitioned according to various subsystems. If an equivalence class is closed, meaning that no state outside the class is accessible from a state within the class, then for long-run analysis that class can be treated as an irreducible Markov chain in its own right: once inside the class, the system cannot leave it. Hence, we will consider long-run dynamics in terms of a single irreducible finite Markov chain.

A key property in the characterization of long-run behavior is periodicity. Since periodicity is a class property, an irreducible Markov chain can be considered to be or not to be aperiodic. A homogeneous Markov chain with finite state space $S=\{1, 2, \ldots, M\}$ is said to possess a stationary distribution (or invariant distribution) if there exists a probability distribution $\pi=(\pi_1, \pi_2, \ldots, \pi_M)$ such that, for any $j\in S$ and for any number r of time steps, $$\pi_j = \sum_{i=1}^{M} \pi_i P_{ij}^r,$$

where $P_{ij}^r$ is the r-step transition probability. Hence, if the initial distribution is or $\pi=(\pi_1, \pi_2, \ldots, \pi_M)$, then the probability of being in state i at time r is equal to $\pi_i$ for all r and the Markov chain is a strictly stationary random process. The Markov chain is said to possess a steady state (limiting) distribution if there exists a probability distribution $\pi=(\pi_1, \pi_2, \ldots, \pi_M)$ such that, for all states i, $j\in S$, $$\lim_{r\to\infty} P_{ij}^r = \pi_j.$$

If there exists a steady-state distribution, then, regardless of the starting state, the probability of the Markov chain being in state i in the long run is $\pi_i$. In particular, for any initial distribution $D^0=(D_1^0, D_2^0, \ldots, D_M^0)$, the state probability $D_i^k$ approaches $\pi_i$ as $k\to\infty$. Relative to the probability vector $\pi$, the vector $D^k$ satisfies $\lim_{k\to\infty} D^k=\pi$. Every irreducible, finite-state, homogeneous Markov chain possesses a unique probability vector $\pi$, with $0<\pi_i<1$, providing the stationary distribution. If the chain is also aperiodic, then $\pi$ also provides the steady-state distribution. Should the chain only be irreducible, and not necessarily aperiodic, then it may not possess a steady-state distribution. A more detailed treatment of the above concepts can be found in most textbooks on stochastic processes.

If the chain has a steady-state distribution in the long run the probability that the chain is in state i may be determined without depending on the initial state. Suppose the states are divided into two classes, $C_1$ and $C_2$. Then we can answer the following question without concern for the initial state: in the long run, what is the probability that the chain is in class $C_1$ (or $C_2$)? Such a question need not be answerable if there does not exist a steady state (if the chain is not aperiodic). An illustrative example is presented in Example 3 below.

Influences of Genes in Probabilistic Boolean Networks

Given a gene $x_i$ and a predictor $f_j^{(i)}$ for that gene, along with the genes used to make the prediction, it is important to distinguish those genes that may have a major impact on the predictor from those that may have only a minor impact. In other words, some (parent) genes may be more important than others in determining the value of a target gene. Many examples of such biased regulation of gene expression are known to biologists. For example, the cell cycle regulator gene p21/WAF1/cipI can be transcriptionally activated by a series of genes p53, smad4, AP2, BRCAI, etc. Among those genes, p53 has the most potent effect.

Suppose the Boolean function $f(x_1, x_2, x_3, x_4) = x_1 \vee x_2 x_3 x_4$ is used as a predictor of some gene, where the symbol $\vee$ is disjunction and $\cdot$ is conjunction. It is easy to see that $x_1$ is a more important variable because setting it to 1 forces the function to be equal to 1 regardless of the other variables. However, if $x_1=0$, the other three variables must cooperate in order to determine the value of the function. The influences of variables on Boolean functions can quantify this notion of importance, while taking into account the joint distribution of the variables.

To define the notion of influence, first consider the partial derivative of a Boolean function with respect to variable $x_j$ ($1 \leq j \leq n$):

$$\frac{\partial f(x)}{\partial x_j} = |f(x) - f(x^{(j)})|$$

where $x^{(j)}$ is the same as x except that the jth component is toggled (from 0 to 1, or from 1 to 0). While this definition uses the real-valued equivalent of a Boolean function and resembles the definition of a real-valued derivative, another standard definition of the partial derivative of a Boolean function f is given by $$\frac{\partial f(x)}{\partial x_j} = f(x^{(j,0)}) \oplus f(x^{(j,1)})$$

where $\oplus$ is addition modulo 2 (exclusive OR) and, $x^{(j,k)} = (x_1, \ldots, x_{j-1}, k, x_{j+1}, \ldots, x_n)$, for k=0, 1. The second definition inherently indicates that the partial derivative is itself a Boolean function. The physical meaning behind the partial derivative of a Boolean function with respect to the ith variable is that, defined on the n−1 dimensional projection of the n-cube, it acts as an indicator of whether or not the function differs along the ith dimension. The partial derivative is 0 if toggling the value of variable $x_j$ does not change the value of the function, and it is 1 otherwise.

The influence of the variable $x_j$ on the function $f$ is the expectation of the partial derivative with respect to the distribution D(x):

$$I_j(f) = E_D\left[\frac{\partial f(x)}{\partial x_j}\right] = Pr\left\{\frac{\partial f(x)}{\partial x_j} = 1\right\} = Pr\{f(x) \neq f(x^{(j)})\} \quad (7)$$

The last expression gives the influence as the probability that a toggle of the jth variable changes the value of the function.

In (standard) Boolean networks, a predictor function $f_i$ is assigned to node $x_i$. Thus, instead of thinking of a variable as influencing the function, one may think of it as influencing the target node or gene. Furthermore, the partial derivative itself is a Boolean function and thus equation (7) can be interpreted as a conditional probability that the value of node $x_i$ is equal to 1, given that the partial derivative was used as a predictor of the value of node $x_i$ $$I_j(x_i) = Pr\left\{X_i = 1 \,\bigg|\, \frac{\partial f_i(x)}{\partial(x_j)} \text{is used as a predictor}\right\} \quad (8)$$

where the notation $I_j(x_i)$ represents the influence of gene $x_j$ on gene $x_i$, given $f_i$ as the predictor (cf. 10). The point of this observation is to show that the same methods and framework that are used for gene predictors in Boolean networks can be used for influences as well, simply by replacing predictors by their partial derivatives.

One step further is the consideration of PBNs. In this case, there may be a number of predictors for each gene, along with their probabilities. As before, let $F_i$ be the set of predictors for gene $x_i$ with corresponding probabilities $c_1^{(i)}, \ldots, c_{l(i)}^{(i)}$. Let $I_k(f_j^{(i)})$ be the influence of variable $x_k$ on the predictor $f_j^{(i)}$. Since many possible predictors can be used for gene $x_i$, we would like to determine the overall influence of gene $x_k$ on gene $x_i$. Thus, the same idea as in equation (21) see example 5 below) can be used, simply by unconditioning on all the partial derivatives of the predictors. Specifically, $$I_k(x_i) = \sum_{j=1}^{l(i)} I_k(f_j^{(i)}) \cdot c_j^{(i)}. \quad (9)$$

This calculation can be performed between all pairs of variables and a n×n matrix $\Gamma$ of influences can be constructed. That is, $\Gamma_{ij} = I_i(x_j)$. We will call 64 the influence matrix. See example 2 below for an example illustrating the computation of the influence of one variable on another, in the context of PBNs.

Random Gene Mutations

Suppose that any gene out of n possible genes, can get mutated with probability p, independently of other genes. In the Boolean setting, this is represented by a flip of value from 1 to 0 or vice versa and directly corresponds to the bit-flipping mutation operator in NK Landscapes, as well as in genetic algorithms and evolutionary computing. For Boolean networks, such random gene perturbations can be implemented with the popular DDLab software. This type of "randomization", namely allowing genes to randomly mutate, is biologically meaningful. Since the genome is not a closed system, but rather has inputs from the outside, it is known that genes may become either activated or inhibited due to external stimuli, such as mutagens, heat stress, etc. Thus, a network model should be able to capture this phenomenon. If p=0, then the model is reduced to a PBN as described herein. If p>0, then we have the following situation. With probability $(1−p)^n$, the transition from one state to another occurs as usual, by one of the randomly selected network realizations while with probability $1−(1−p)^n$, the state will change due to random bit mutation(s).

Random gene mutations may be framed as follows. Suppose that at every step of the network, we have a realization of a so-called random mutation vector $\gamma \in \{0,1\}^n$. If the i-th component of $\gamma$ is equal to 1, then the i-th gene is flipped, otherwise it is not. In general, $\gamma$ need not be independent and identically distributed (i.i.d.), but we will assume this for now on for simplicity. The generalization to the non-i.i.d. case is conceptually straightforward. Thus, we will suppose that $\Pr\{\gamma_i=1\}=E[\gamma_i]=p$ for all $i=1, \ldots, n$. Thus, $\Pr\{\gamma=(0, \ldots, 0)\}=(1-p)^n$.

Let $x=(x, \ldots, x_n)$ be the state of the network (i.e. values of all the genes) at some given time. Then, the next state $x'$ is given by $$x' = \begin{cases} x \oplus \gamma, \text{ with probability } 1 - (1-p)^n \\ f_k(x_1, \ldots, x_n), \text{ with probability } (1-p)^n \end{cases} \quad (10)$$

where $\oplus$ is component-wise addition modulo 2 and $f_k(x_1, \ldots, x_n)$, $k=1, 2, \ldots, N$, is the transition function representing a possible realization of the entire PBN. In other words, equation (10) states that if no genes are mutated, the standard network transition function will be used, whereas if at least one mutation does occur, then the next state will be determined according to the genes that are mutated. An important observation to make here is that for $p>0$, any state of the network becomes accessible from any other state, due to the possibility of any combination of random gene mutations.

This is exemplified in following proposition. Proposition: For $p>0$, the Markov chain corresponding to the PBN is ergodic. Since there are only a finite number of states, ergodicity is equivalent to the chain being aperiodic and irreducible. First, by virtue of equation (10), we can note that the Markov state transition matrix has no zero entries except possibly on the diagonal, the latter corresponding to the case when there does not exist a network transition function $f_k$ ($k=1, 2, \ldots, N$) such that $f_k(x)=x$. This immediately implies that the chain is irreducible, since all states communicate. Indeed, let x be such a state (i.e. for which $f_k(x) \neq x$ for all $k=1, 2, \ldots, N$) and let $y \neq x$ be any other state. The probability of transitioning from x to y is positive as is the probability of going from y back to x. Therefore, there is a positive probability that x is accessible from itself in just two steps. Using the same reasoning, the process may return to the same state after any number of steps, except possibly after one step, implying that the chain is also aperiodic.

The fact that a Markov chain is ergodic implies that it possesses a steady-state distribution equal to the stationary distribution, which may be estimated empirically simply by running the network for a sufficiently long time and by collecting information about the proportion of time the process spends in each state. The convergence rate, however, may depend on the parameter p. A simulation-based analysis of the network involving gene mutation may require one to compute the transition probability $A(x,x')=\Pr\{(x_1, \ldots, x_n) \to (x'_1, \ldots, x'_n)\}$ between any two arbitrary states of the network. This is exemplified in Theorem 1 of the attached appendix.

If the mutation vector $\gamma$ is not identically distributed (i.e. some genes are more likely to get flipped), then the above transition probabilities become slightly more complicated, requiring products of individual probabilities $\Pr\{\gamma_i=1\}$. The transition probability between two different states cannot be zero so long as $p>0$.

A practical benefit of the randomization afforded by gene mutation is that it empirically simplifies various computations involving PBNs. For example, consider the computation of influence $I_k(f_j^{(i)})$ of gene $x_k$ on the predictor function $f_j^{(i)}$, as given in equation (7). The computation of influence of a gene on the predictor entails computing the joint distribution $D(x)$ of all the genes used by that predictor, in order to compute the expectation of the partial derivatives of the predictors. This distribution, however, should be consistent with the model itself. For example, if we wish to quantify "long-term" influence, we need to obtain the stationary distribution of the Markov chain corresponding to the PBN. Obtaining these long run probabilities, however, may be problematic from an empirical point of view, since the Markov chain may consist of a number of irreducible subchains and these probabilities will depend on the initial starting state. In other words, depending on where we start the process, we may end up in different irreducible subchains. Obtaining long-run behavior directly from the state-transition matrix A may also be impractical even for moderate sizes of PBNs, thus requiring simulation-based analysis.

The assumption of random gene mutation, described above, solves this problem by ridding us of the dependence on the initial starting state. Since all states communicate the steady-state distribution is the same as the stationary distribution and by letting the process run for a sufficiently long time. we can empirically compute the distribution $D(x)$ simply by keeping track of the proportion of time each combination of values of the genes in the domain of the predictor occurs. For example, if the predictor is a function of some given three variables, then we simply have to tabulate the frequency of appearance of each of the 8 combinations of these three variables to obtain the necessary distribution in order to compute the influence on that predictor.

PBNs for Intervention

One of the various goals of developing models such as PBNs is the identification of potential drug targets in cancer therapy. A random gene perturbation may cause the real regulatory network to transition into an undesirable cellular state, which itself will be stable under most subsequent gene perturbations. One of the challenges is determining which genes would be good potential candidates for intervention in order to reverse the effects or force the regulatory network to transition to another desirable stable state. Thus, it is important not only to study the effects of gene perturbation, especially on long run network behavior, but also to develop tools for discovering intervention targets. While distinguish between random gene perturbation and intentional gene intervention in the discussion this far, the PBN model class allows us to take a unified viewpoint.

One can consider the effects of deliberately affecting a particular gene by means of intervention. One of the various goals of PBN modeling is the determination of possible intervention targets (genes) such that the network can be persuaded if not forced to transition into a desired state or set of states. Whereas, in Boolean networks, attractors are hypothesized to correspond to functional cellular states, in PBNs, this role is played by irreducible subchains. When the probability of mutation, p, is equal to zero, a PBN is unable to escape from an irreducible subchain, implying that the cellular state cannot be altered. When p becomes positive, there is a chance that the current cellular state may switch to another cellular state by means of a random gene perturbation. Clearly, perturbation of certain genes is more likely to achieve the desired result than that of some other genes. Our goal, then, is to discover which genes are the best potential lever points in the sense of having the greatest possible impact on desired network behavior so that we can intervene with them by changing their value (1 or 0) as needed. Typically, one may wish to intervene with as few genes as possible in order to intervene in a network.

Figure 5:
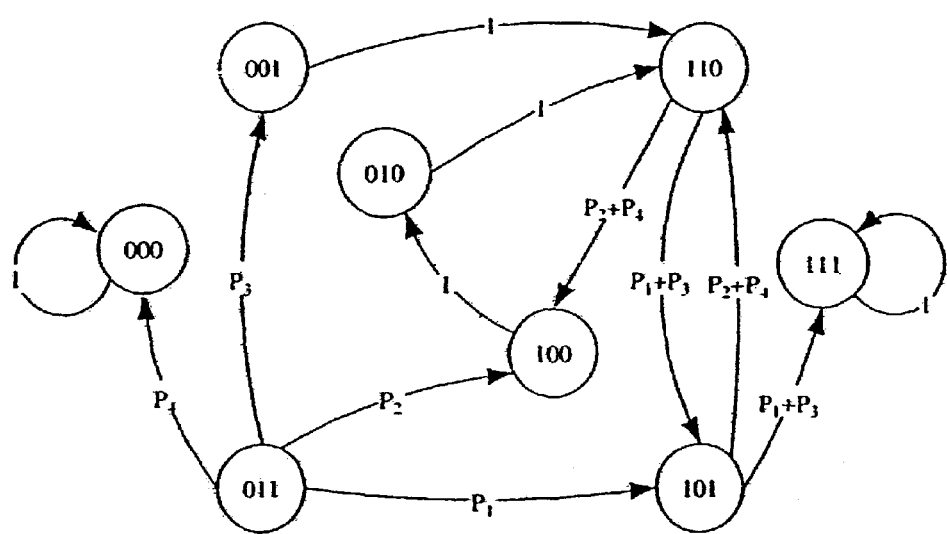
FIG. 5 illustrates an exemplary state transition diagram.

Suppose the state transition diagram of the Markov chain corresponding to the PBN in Example 1 is shown in FIG. 5. For the predictor probabilities given in Example 1, the probabilities of the four possible network realizations are: $P_1=0.3$, $P_2=0.3$, $P_3=0.2$, and $P_4=0.2$. Suppose that we are currently in state (111) and wish to eventually transition to state (000). Finally, let us assume, for the moment, that the probability of random perturbation is zero (p=0). The question is, with which of the three genes, $x_1$, $x_2$, or $x_3$, should we intervene such that the probability is greatest that we will end up in (000). By direct inspection of the diagram in FIG. 5, we can see that if we make $x_1=0$, then with probability $P_4$32 0.2, we will transition into (000) whereas if we make $x_2=0$ or $x_3=0$, it will be impossible for us to end up in (000) and with probability 1, we will eventually come back to (111), where we started. In other words, the network will be resistant to perturbations of the second or third genes and will eventually maintain the same state. Thus, the answer to our question in this rather simple example is that only by intervening with gene $x_i$ do we have a chance of achieving our goal. In order for us to be able to answer such questions in general, we need to develop several tools.

When p>0 the entire Markov chain is ergodic and thus, every state will eventually be visited. Thus, the question of intervention should be posed in the sense of reaching a desired state as early as possible. For instance, in the example considered above, if p is very small and we are in state (111), then it will, be a long time until we reach (000) and setting $x_1=0$ is much more likely to get us there faster. We are, therefore, interested in the probability $F_k(x,y)$ that, starting in state x, the first time the PBN will reach some given state y will be at time k. This may be referred to as the first passage time from state x to state y. A related measure of interest is the mean first passage time from state x to state y, defined as $$M(x, y) = \sum_k k f_k(x, y) \tag{11}$$

This measure tells us how long, on the average, it will take to get from state x to state y.

One may see that for k=1, $F_k(x,y)=A(x,y)$, which is the transition probability from x to y. For k≥2, it is also straightforward to show that $F_k(x,y)$ satisfies $$F_k(x, y) = \sum_{z \in \{0,1\}^n - \{y\}} A(x, y) F_{k-1}(z, y) \tag{12}$$

Every required entry of the matrix A can be computed directly using Theorem 1, see attached appendix.

Figure 6:
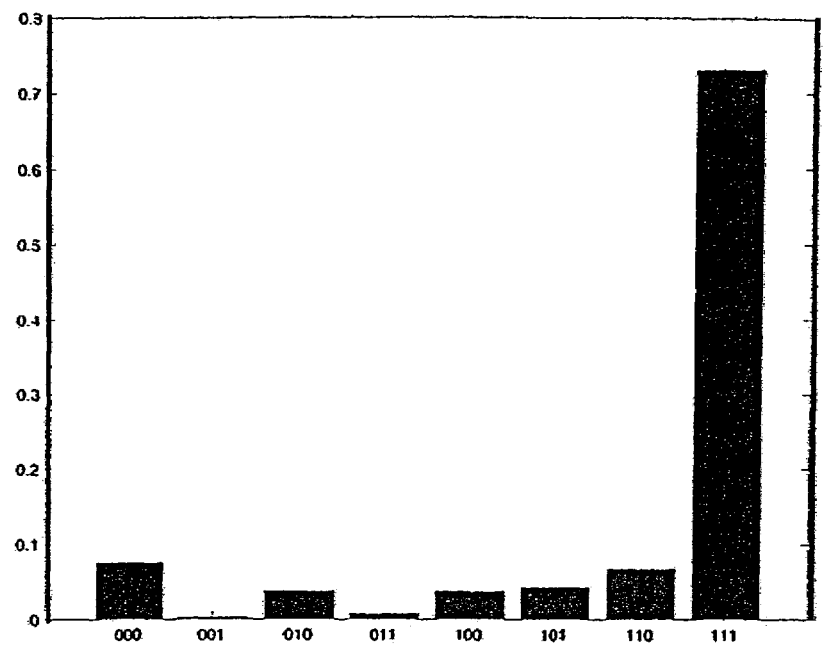
FIG. 6 illustrates an exemplary steady-state distribution.
Figure 7:
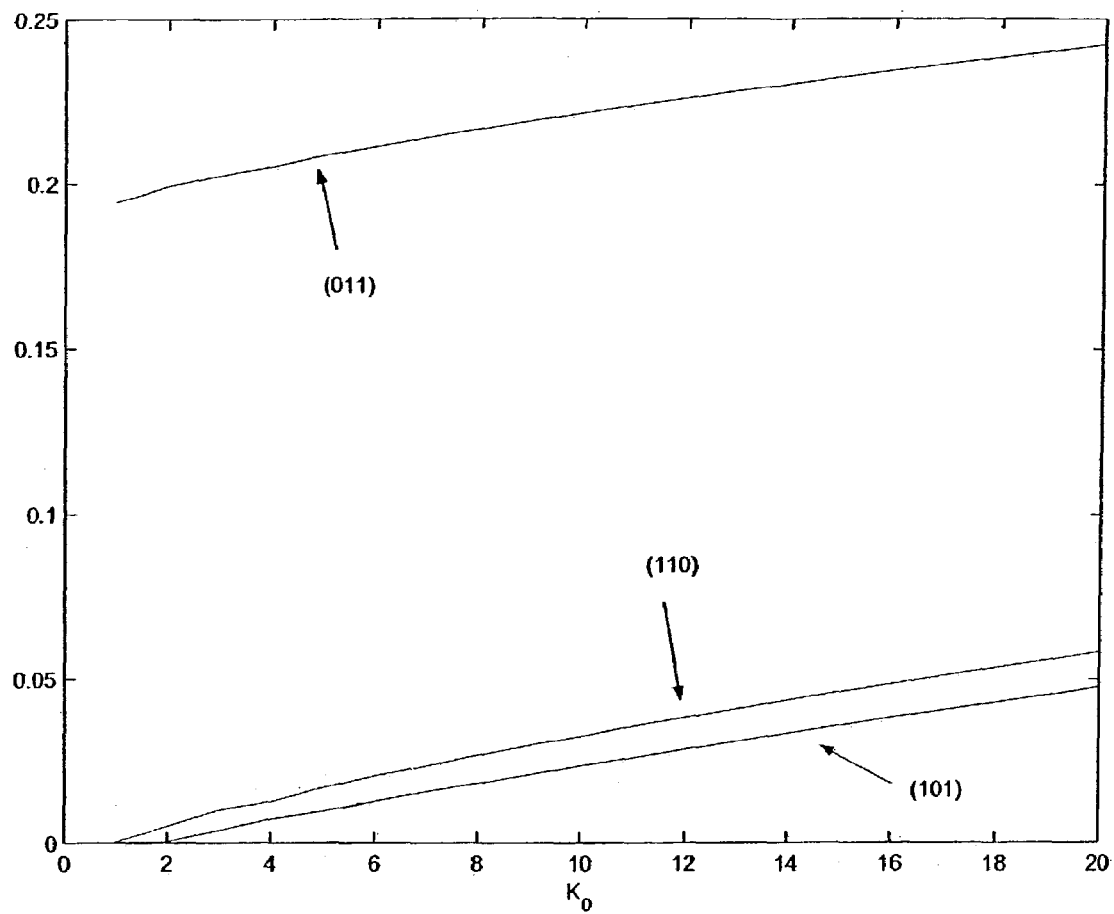
FIG. 7 illustrates an exemplary plot of $H_{K_o}(x,y)$ for $K_o = 1, \ldots, 20$.

An illustrative example of this computation is as follows. Suppose, as before, that p=0.01. Then, the steady-state distribution is shown in FIG. 6. As expected, the PBN spends much more time in state (111) than in any other state. In fact, more than 70% of the time is spent in that state. Let our starting state x be (111) and the destination state y be (000), as before. The question with which we concern ourselves is whether we should intervene with gene $x_1$, $x_2$, or $x_3$. In other words, we would like to compute $F_k$ ((011), (000)). $F_k$ ((101), (000)), and $F_k$ ((110), (000)), where the states are written in their binary representations. We may assess our results by plotting $$H_{K_0}(x, y) = \sum_{k=1}^{K_0} F_k(x, y) \tag{13}$$

for the states x of interest and for a sufficiently large $K_0$. The intuition behind this approach is the following. Since the events {the first passage time from x to y will be at time k} are disjoint for different values of k, the sum of their probabilities for k=1, ..., $K_0$ is equal to the probability that the network, starting in state x, will visit state y before time $K_0$. As a special case, when $K_0=\infty$, this is equal to the probability that the chain ever visits state y, starting at state x, which of course is equal to 1, since our chains are ergodic if p>0. FIG. 7 shows the plots of $H_{K_0}$ (x,y) for $K_0=1, ..., 20$ and for the three states of interest, namely, (011), (101), and (110).

The plots indicate that if we start with state (011), we are much more likely to enter state (000) sooner than if we start with states (110) or (101). For example, during the first 20 steps, we have an almost 25% chance of entering (000) if we start with (011), whereas if we start with (110) or (101), we only have about a 5% chance. This, in turn, indicates that we should intervene with gene $x_1$ rather than with gene $x_2$ or $x_3$. Of course, in this rather simple example, we could have discerned this by visual inspection of FIG. 5, but for larger networks, this method provides a tool for answering these kinds of questions.

In biology, there are numerous examples when the (in) activation of one gene or protein can lead much quicker (or with a higher probability) to a certain cellular functional state or phenotype than the (in)activation of an other gene or protein. For instance, let's use a stable cancer cell line as an example. Without any intervention, the cells will keep proliferating. Let us assume that the goal of the intervention is to push the cell into programmed cell death (apoptosis). Let us further assume that we will achieve this intervention with two gene candidates: p53 and telomerase. The p53 gene is the most well-known tumor suppressor gene, encoding a protein that regulates the expression of several genes such as Bax and Fas/APO1 that function to promote apoptosis and p21/WAF1 that functions to inhibit cell growth. The telomerase gene encodes telomerase, which maintains the integrity of the end of chromosomes (telomeres) in our germ cells, which are responsible for propagating our complete genetic material to the following generation, as well as progenitor cells, which are responsible for replenishing our cells during the normal cell turnover (homeostasis). In somatic cells, the telomerase gene is turned off, resulting in telomere shortening each tune the cell divides—a key reason for the limited life span of our normal cells. In the majority of tumor cells, telomerase is activated, which is believed to contribute to the prolonged life-span of the tumor cells and worsened prognosis for the cancer patients. Extensive experimental results indicate that when p53 is activated in the cells, for example, in response to radiation, the cells undergo rapid growth inhibition and apoptosis in as short as a few hours. In contrast, inhibition of the telomerase gene also leads to cell growth inhibition, differentiation, and cell death, but only after cells go through a number of cell divisions (allowing telomere shortening), which takes a longer time to occur than via p53.

Another valuable computational tool may be the mean first passage times given in equation (11). The best candidate gene for intervention will typically be the one that results in the smallest mean first passage time to the destination state. Using the same example as above, we have computed the three mean first passage times corresponding to the perturbation of genes $x_1$, $x_2$, and $x_3$. These are equal to 337.51, 424.14, and 419.20, respectively. Since the first one is the smallest, this again supports that gene $x_1$ is the best candidate for intervention.

To summarize, we simply generate different states $x^{(i)} = x \oplus e_i$, $i=1, \ldots, n$, where $e_i$ is the unit binary vector with a 1 in the i-th coordinate, by perturbing each of the n genes and compute $H_{K_O}(x^{(i)}, y)$ for some desired destination state y and constant $K_O$, Then, the best gene for intervention is the one for which $H_{K_O}(x^{(i)}, y)$ is maximum. That is, given a fixed $K_O$, the optimal gene $x_{i_{opt}}$, satisfies $$i_{opt} = \arg\max_i H_{K_o}(x^{(i)}, y) \quad (13)$$

Alternatively, by minimizing the mean first passage times, the optimal gene satisfies $$i_{opt} = \arg\max_i M(x^{(i)}, y). \quad (14)$$

Another related approach to the one in (13) might be to first fix a probability $h_0$ and wait until one of the $H_{K_O}(x^{(i)}, y)$ reaches it first. Note that due to ergodicity, for every state $x^{(i)}$, there will always be a $K_0^{(i)}$ large enough such that $H_{K_0^{(i)}}(x^{(i)}, y) > h_0$. In that sense, the optimal gene for intervention $x_{i_{opt}}$ is one for which $$i_{opt} = \arg\min_i \min_{K_0^{(i)}} \left\{ K_0^{(i)} : H_{K_0^{(i)}}(x^{(i)}, y) > h_0 \right\}. \quad (15)$$

At first glance, it might appear as if both approaches, (13) and (15), may yield the same answer, since FIG. 7 seems to suggest that the plots do not intersect and that if one of them is maximum for a given $K_0$, it will be the first to reach any fixed $h_0$ thereafter. While it is true that for sufficiently large $K_0$, the plots will not intersect, this is not true for smaller values of $K_0$.

Figure 8:
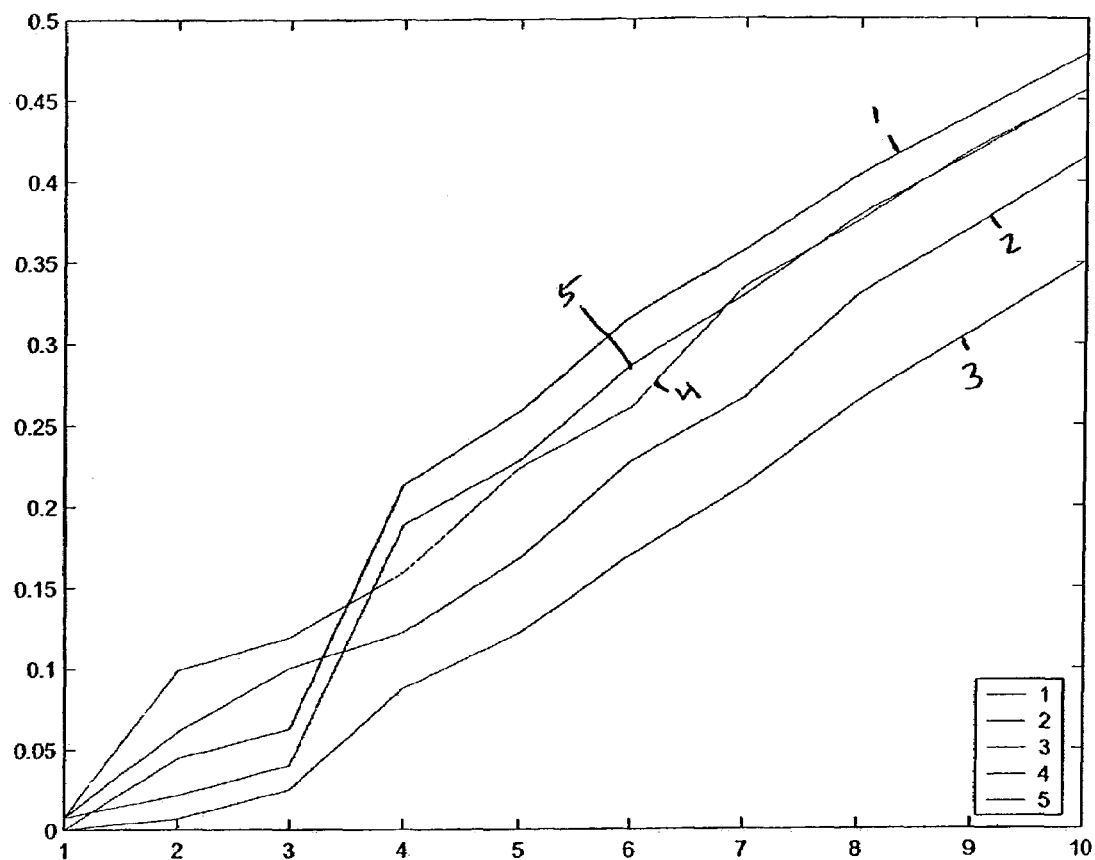
FIG. 8 illustrates an example plots of $H_{K_o}(x^{(i)}, y)$.

As an example, we have generated a random PBN consisting of 5 genes and p=0.1. FIG. 8 shows the 5 plots of $H_{K_O}(x^{(i)}, y)$, each one corresponding to an intervention with one of the genes. In this example, x=(11111) and y=(10100). As can be seen, the two approaches discussed above differ for small values of $K_0$. For example, if we fix a probability $h_0$=0,1, then gene $x_4$ is the best candidate for intervention, since $H_{K_O}(x^{(4)}, y) > h_0$ for $K_0$=2. However, as can be seen from the figure, after 4 steps of the network, gene $x_1$ is more likely to drive the network to the desired state. The choice of which approach to use should be made available to the practitioner, since the criteria imbedded in equations (13) and (15) have underlying different interpretations. The first may maximize the probability of reaching a particular state before a certain fixed time while the second may minimize the time needed to reach a certain state with a given fixed probability. These two approaches are complementary and may be used in conjunction. The approach in equation (14) based on minimizing mean first passage times is another simple alternative. First passage times are discussed further below, when discussing sensitivity analysis of PBNs.

Sets of States, Avoidance of States, and Permanent Intervention

The notion of intervention has been discussed in terms of a single starting state and a single destination state. However, one may often be more interested in the same types of questions, but concerning sets of states. For example, two different sets of states may correspond to different functional cellular states, such as proliferation or quiescence, much in the same way attractors play this role in standard Boolean networks. In PBNs this role is typically played by irreducible subchains when no mutations can occur (p=0). In other words, once the network enters an irreducible subchain (cf. attractor), it can't escape. When the mutation probability is positive, there are no longer any irreducible subchains (see Proposition 1), but the sets of states that correspond to these irreducible subchains when p=0 still represent the functional states of the organism that is being modeled - there is now simply a probability of escaping due to random mutations. Those sets of states that correspond to irreducible subchains when p=0 could be referred to as implicitly irreducible subchains. They are essentially islands of states and the probability of mutation controls the amount of bridges between these islands. When p=0, there are no bridges, and when p becomes larger, it becomes easier to travel between the islands.

Going back to the question of intervention, one may be interested in posing it as follows. Given a set of states X, what gene is the best candidate for intervention if we want to end up in the set of states Y? The question may be posed in the sense of either (13), (14), or (15). The mathematical framework typically does not really change when talking about sets of states. For example, if X={x} consists of just one state, but Y is a set comprised of many states, then the first passage probabilities $F_k(x,y)$ may simply be summed over all states y∈Y and we can define $F_k(x,Y) = \Sigma_{y \in Y} F_k(x, y)$. Then, the same approaches as discussed above to find the best gene for intervention can be used.

The situation when X is comprised of a number of states is conceptually a bit more complicated, since now, the starting set of states X, rather than just one starting state x, represents a type of uncertainty in our knowledge of the current state of the network. That is, we may not know exactly in what state the network is in at a particular time, but we may know that it is in a certain set of states. This may be relevant not only from an experimental perspective, as it may be difficult to determine precisely the current state at a given time, but perhaps more importantly, we may not be interested in restricting ourselves just to one state, but rather consider a whole set of states X that is believed to correspond to the current functional cellular state.

Consequently, a gene that may typically be the best candidate for intervention for one of the starting states in X may not be the best for another state in X. Therefore, the approach in such a case is to combine the individual results for all states x∈X, but weigh them by their respective probabilities of occurrence. The latter is furnished by the steady-state probabilities $\pi_x$. In other words, we can define $$F_k(X, Y) = \frac{\sum_{x \in X} \sum_{y \in Y} F_k(x, y) \cdot \pi_x}{\sum_{x \in X} \pi_x} \quad (16)$$

to be the first passage probability from a set X to a set Y.

In addition to reaching a desired state or set of states, we may also be interested in avoiding a state or set of states. This is quite natural in terms of inducing a network not to enter into some sets of states corresponding to unwanted functional cellular states (e.g., proliferation). This goal is in a sense complementary to what has been described above in terms of reaching a desired state either as soon as possible with a given probability or with as high probability as possible, before a given time. For example, in equation (14), our goal was to minimize the mean first passage time to a destination state. In order to avoid a destination state, we simply have to maximize the mean first passage time to that state. So, the underlying mechanism may be quite the same and we will not give a separate example illustrating the avoidance of states. It may be possible that performing no intervention whatsoever is the best option, regardless of whether we want to reach or avoid a state or set of states. In other words, depending on the network as well as on the starting and destination states or sets of states, it may be the case that not intervening with any gene is optimal in terms of the criteria given in (13), (14), or (15).

In an exemplary model, the type of intervention and mutation that we have considered could be termed transient intervention or mutation. That is, the effect on a gene, whether by random perturbation or forced intervention, is applied at only one time point and the network itself is responsible for determining the values of that gene thereafter. It could be said that the effect has the potential to be reversed by the network itself. For example, in FIG. 5, if we are in state (111) and the second gene changes value, resulting in (101), at the next time step, regardless of where the network transitions, (110) or (111), the second gene will always get changed back to 1 again. Since in that example (111) is an absorbing state, the network will eventually return to it, and the perturbation or intervention—whatever the means was of changing the second gene—will have been compensated by the network itself. This inherent resistance to perturbations is a key factor for stability and robustness of PBNs.

In other embodiments one may also consider a permanent intervention or mutation. In this scenario, a gene changes value and remains at that value forever. From a genetic perspective, permanent intervention is achieved through removing a gene or transplanting a gene, as done in gene therapy. From a network perspective, the permanent intervention (or mutation) of a gene may reduce the state space by half, since all the states in which that gene is not equal to the fixed value cannot appear. The rest of the genes are predicted as usual, via the Boolean functions and their selection probabilities $c_j^{(i)}$ remain unaltered. The Boolean function corresponding to the fixed gene is the identity function (0 or 1) with selection probability 1.

Permanent intervention by gene manipulation is used by both nature and humans. It is an efficient way to generate mutations and also hoped to be an efficient way for correcting mutations (therapy). Perhaps the best example for the first scenario is viral infection. Let us use Simian Virus 40 (SV40) as an example. SV40 virus was discovered in the 1950s during the development of vaccine for poliovirus. It was found that SV40 could transform monkey kidney cells and develop tumors when injected into rodents. SV40 was not believed to cause tumor in human cells, however, SV40 DNA was found in some human brain tumors in recent years suggesting that SV40 may have a tumorigenic effect in humans too, although with a long latent period. Extensive research has been carried out to elucidate how SV40 causes cancer in mouse cells. Though SV40 does not have a big genome, one of the most important proteins encoded by SV40 is large T-antigen. Large T antigen interacts with host cell molecules and triggers a series of events that are beneficial for the viral replication and bad for the host cells. For example, T-antigen inactivates the functions of p53, which may be the key mechanism for the tumorigenic effect of SV40 T-antigen. We should point out that SV40 T-antigen also interacts with other molecules such as retinoblastoma (Rb)—an important protein the activation of which inhibits DNA synthesis. From a network perspective, the permanent mutation caused by SV40 T-antigen may permanently alter the dynamics of the network, causing it to shift into a set of states associated with tumorigenesis. To further prove that T-antigen itself is sufficient to cause this effect, T-antigen was transplanted into the mouse brain using a tissue-specific transgenic mouse model (second scenario, man-made event). As expected, brain tumors were found in many of the transgenic mice. Since SV40 DNA was detected in some human brain tumors, one cannot help but to speculate that SV40 may be causing human brain tumors too.

From the point of view of man-made intervention, it may be that permanent rather than transient intervention is the only way to reach a desired set of states. That is, it may be the case that the network is so resistant to transient intervention of any gene, that it will be extremely unlikely for the network to ever reach (or avoid) the desired states. Permanent intervention, though less desirable as it introduces permanent changes to the network, may be the only alternative to reach a set of states with a sufficiently high probability. The question, as before, is what genes are the most likely "lever points" for controlling the global behavior of the network.

For example, based on what is known, p53 is one such gene. This is clearly demonstrated by the fact that p53 gene deletion or mutation (permanent mutation) is one of the most frequent genetic changes in cancers. Removing p53 genes from mouse through embryonic stem cell gene knock-out technology, researchers generated the p53 null mice. The mouse can be born normally and develop into adult normally, but develop cancers in most of the mice at 4.5 months. So p53 may be an important lever gene for regulation of homeostasis—a delicate balance between cell growth and cell death. Thus, it may not be surprising that p53 is often selected as a therapeutic target for permanent intervention. In cultured cells, the introduction of p53 back to p53-null cells leads to cell growth inhibition or cell death. Thus one properly chosen lever gene has the potential to lead the network into a specific implicitly irreducible subchain (cf. attractor in standard Boolean networks), p53 gene is also being used in gene therapy, where the target gene (p53 in this case) is cloned into a viral vector (adenovirus vector is a common one). The modified virus serves as a vehicle to transport p53 gene into the tumor cells to generate a permanent intervention.

Sensitivity of Stationary Distributions to Gene Mutations

In this example the question of sensitivity of the stationary distributions to random gene perturbations is addressed.

This example characterizes the effect of perturbations on long-term network behavior. It is clear that whatever is meant by sensitivity, it will no doubt depend on the probability of random mutation, p. The general question is: if we perturb the transition probabilities, how much will the stationary distributions, or equivalently, the limiting probabilities change? This question has generally been addressed in the area known as perturbation theory of stochastic matrices. If A and Ã=A−E are the original and perturbed Markov matrices, where E represents the perturbation, and π and π̃ are their respective stationary distributions, then most results are of the form $$\|\tilde{\pi} - \pi\| \leq \kappa \|E\|, \text{ or } \left|\frac{\pi_j - \tilde{\pi}_j}{\pi_j}\right| \leq \kappa_j \|E\|,$$

for some matrix norm $\|\cdot\|$ and $\kappa$, $\kappa_j$ are called condition numbers and are used as measures of sensitivity. Recently, a new approach to measure the sensitivity of the Markov chain to perturbations, in terms of mean first passage times, has been proposed by Cho and Meyer. This approach has the advantage in that it does not require computing or estimating the condition numbers. The result is presented in the attached appendix under Theorem 2.

II. Boolean Networks—Models of Gene Regulatory Networks

One of the objectives of Boolean network modeling is to study generic coarse-grained properties of large genetic networks and the logical interactions of genes, without knowing specific quantitative details. The biological basis for the development of Boolean networks as models of genetic regulatory networks lies in the fact that during regulation of functional states, the cell exhibits switch-like behavior, which is important for cells to move from one state to another in a normal cell growth process or in situations when cells need to respond to external signals, many of which are detrimental. Let us use cell cycle regulation as an example. Cells grow and divide. This process is highly regulated; failure to do so results in unregulated cell growth in diseases such as cancer. In order for cells to move from the G1 phase to the S phase, when the genetic material, DNA, is replicated for the daughter cells, a series of molecules such as cyclin E and Cyclin Dependent Kinase 2 (cdk2) work together to phosphorylate the Retinoblastoma (Rb) protein and inactivate it, thus releasing cells into the S phase. Cdk2/cyclin E is regulated by two switches: the positive switch complex called Cdk Activating Kinase (CAK) and the negative switch p21/WAF1. The CAK complex can be composed of two gene products: cyclin H and cdk7. When cyclin H and cdk7 are present, the complex can activate cdk2/cyclin E. A negative regulator of cdk2/cyclin E is p21/WAF1, which in turn can be activated by p53. When p21/WAFI binds to cdk2/cyclin E, the kinase complex is turned off. Further, p53 can inhibit cyclin H, a positive regulator of cyclin E/cdk2. This negative regulation is an important defensive system in the cells. For example, when cells are exposed to mutagen, DNA damage occurs. It is to the benefit of cells to repair the damage before DNA replication so that the damaged genetic materials do not pass onto the next generation. An extensive amount of work has demonstrated that DNA damage triggers switches that turn on p53, which then turns on p21/WAF1. p2I/WAFI then inhibits cdk2/cyclin E, thus Rb becomes activated and DNA synthesis stops. As an extra measure, p53 also inhibits cyclin H, thus turning off the switch that turns on cdk2/cyclin E. Such delicate genetic switch networks in the cells is the basis for cellular homeostasis.

Figure 9:
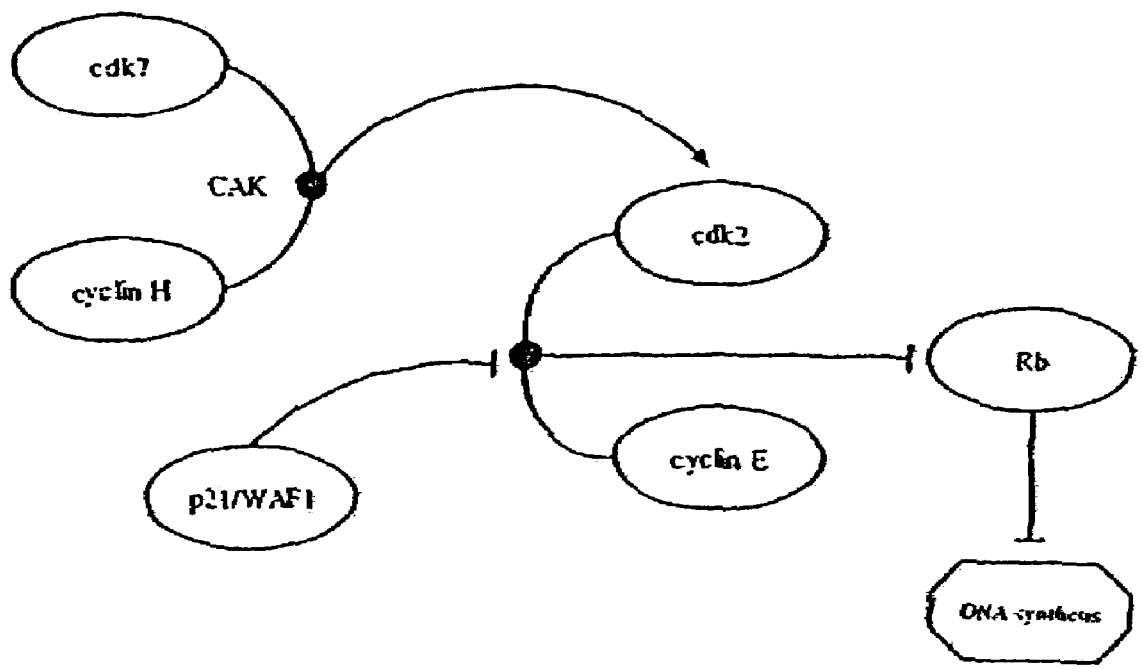
FIG. 9 illustrates an example of the effects of cdk7/cyclin H, cdk2/cyclin E, and p21/WAFI on Rb.

For purposes of illustration, let us consider a simplified diagram, shown in FIG. 9, illustrating the effects of cdk7/cyclin H, cdk2/cyclin E, and p21/WAFI on Rb. Thus, p53 and other known regulatory factors are not considered.

Figure 10:
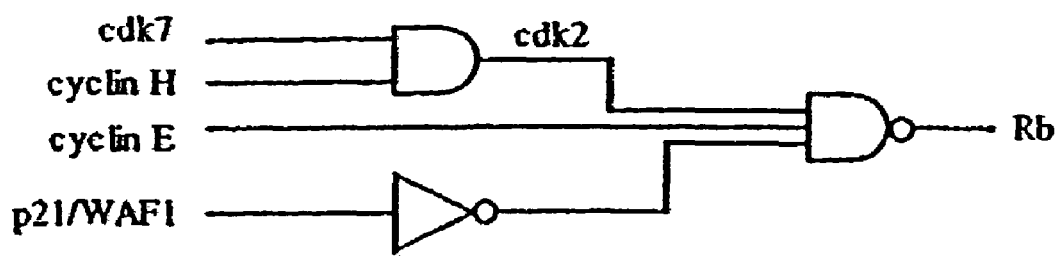
FIG. 10 illustrates an example of a logic circuit diagram of the activity of Rb (on or off) as a Boolean function.

While this diagram represents the above relationships from a pathway perspective, we may also wish to represent the activity of Rb in terms of the other variables in a logic based fashion. FIG. 10 illustrates an example of a logic circuit diagram of the activity of Rb (on or off) as a Boolean function of four input variables: cdk7, cyclin H, cyclin E, and p21/WAF1. Note that cdk2 is shown to be completely determined by the values of cdk7 and cyclin H using the AND operation and thus, cdk2 is not an independent input variable. Also, in FIG. 9, p21/WAF1 is shown to have an inhibitive effect on the cdk2/cyclin E complex, which in turn regulates Rb, while in FIG. 10, we see that from a logic-based perspective, the value of p21/WAF1 works together with cdk2 and cyclin E to determine the value of Rb.

A Boolean network $G(V,F)$ may be defined by a set of nodes $V=\{x_1, \ldots, x_n\}$ and a list of Boolean functions $F\{f_1, \ldots, f_n\}$. A Boolean function $f_i(x_{i_1}, \ldots, x_{i_k})$ with k specified input nodes is assigned to node $x_i$. In general, k could be varying as a function of i, but without loss of generality, we may define it to be a constant equal to n and allowing the unnecessary variables (nodes) in each function to be fictitious. For a function $f$, the variable $x_i$ is fictitious if $f(x_1, \ldots, x_{i-1}, \ldots, x_n) = f(x_1, \ldots, x_{i+1}, \ldots, x_n)$ for all $x_1, \ldots, x_{i-1}, x_{i+1}, \ldots, x_n$. A variable that is not fictitious is called essential. Each node $x_i$ represents the state (expression) of gene i, where $x_i=1$ means that gene i is expressed and $x_i=0$ means it is not expressed. The list of Boolean functions F represents the rules of regulatory interactions between genes. That is, any given gene transforms its inputs (e.g., regulatory factors that bind to it) into an output, which is the state or expression of the gene itself. All genes (nodes) are updated synchronously in accordance with the functions assigned to them and this process is then repeated. The artificial synchrony simplifies computation while preserving the qualitative, generic properties of global network dynamics.

Figure 11:
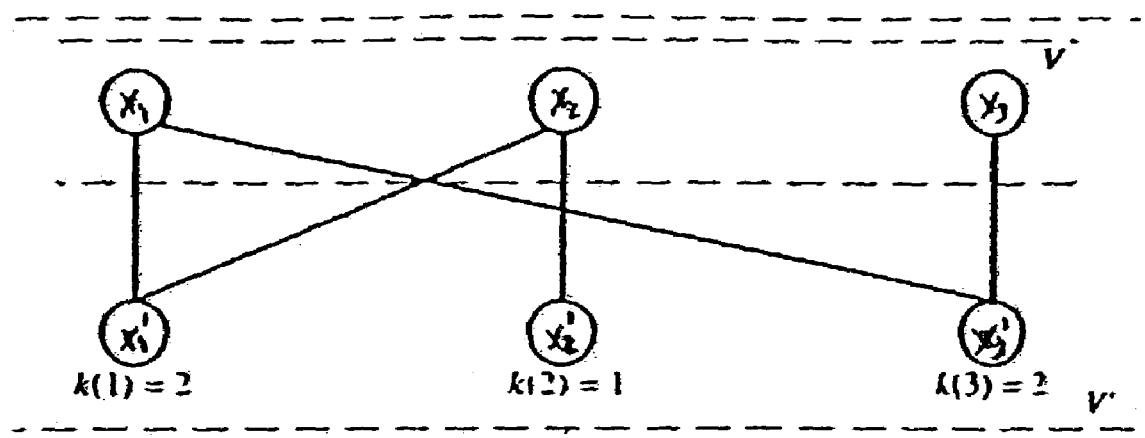
FIG. 11 illustrates an example of a wiring diagram for n=3.

To capture the dynamic nature of these networks, it may be useful to consider a wiring diagram $G'(V',F')$. Let $k(i)$ be the number of essential variables of function $f_i$ in F. We then construct n additional nodes $x'_1, \ldots, x'_n$ and for each $i=1, \ldots, n$, we draw an edge from $x_{ij}$ to $x'_i$, for each $1 \leq j \leq k(i)$. Then, $V'=\{x_1, \ldots, x_n, x'_1, \ldots, x'_n\}$ and the list F' is actually the same as F, but containing the same functions being assigned to nodes $x'_1, \ldots, x'_n$ (with inputs from V) while the functions assigned to $x_1, \ldots, x_n$ are just the trivial identity functions, e.g., $f(x_i)=x_i$. In other words, $x'_i=f_i(x_{i_1}, \ldots, x_{i_{k(i)}})$ and thus, the expression pattern $(x_1, \ldots, x_n)$ corresponds to the states of the genes at time t (INPUT) and the pattern $(x'_1, \ldots, x'_n)$ corresponds to the states of the genes at time t+1 (OUTPUT). An example of a wiring diagram for n=3 is shown in FIG. 11. Collectively, the states of individual genes in the genome form a Gene Activity Profile (GAP).

Consider the state space of a Boolean network with n genes. Then, the number of possible GAPs is equal to $2^n$. For every GAP, there is another successor GAP into which the system transitions in accordance with its structural rules as defined by the Boolean functions. Thus, there is a directionality that is intrinsic to the dynamics of such systems. Consequently, the system ultimately transitions into attractor states. The states of the system that flow into the same attractor state make up a basin of attraction of that attractor. Sometimes, the system periodically cycles between several limit-cycle attractors. It is interesting to note that such behavior even exists for some infinite networks (networks with an infinite number of nodes), such as those in which every Boolean function is the majority function.

Although the large number of possible GAPs would seem to preclude computer-based analysis, simulations show that for networks in which most Boolean functions have few essential variables, only a small number of GAPs actually correspond to attractors. Since other GAPs are unstable, the system is normally not found in those states unless perturbed.

Dynamics of Boolean Networks

Since Boolean networks are completely deterministic, so are their dynamics. The only randomness that may exist lies entirely in the selection of the initial starting state of the network. This can be captured by considering the joint probability distribution of all the genes. In order for us to have a useful probabilistic description of the dynamics of such systems, it is necessary to consider joint probabilities of all Boolean functions corresponding to all the nodes because even after one step of the network, the nodes become dependent, regardless of assumptions on the initial distribution.

To this end, suppose we are given a Boolean network $G(V,F)$ containing n nodes (genes) $x_1, \ldots, x_n$, and an initial joint probability distribution $D(x)$, $x \in \{0,1\}^n$, over the n-dimensional hypercube. We are interested in computing the joint probability of every node after one step of the network. One can see that $$Pr\{f_1(x) = i_1, f_2(x) = i_2, \ldots, f_n(x) = i_n\} = \sum_{x \in \{0,1\}^n : f_k(x) = i_k, k=1,\ldots,n} D(x) \quad (17)$$

where $i_k \in \{0,1\}$. Equation (17) can then be used in an iterative fashion, following the dynamic nature of the system. In other words, the computed joint distribution $Pr\{f_k(x) = i_k, k=1, \ldots, n\}$ can be used in place of $D(x)$ to compute the joint distribution at the next time point. This defines the iterative system $$D^{t+1} = \Psi(D^t) \quad (18)$$

where the mapping $\Psi:[0,1]^{2^n} \to [0,1]^{2^n}$ is implicitly defined by (17). In fact, $\Psi$ is an affine mapping. To see this, let $D^t$ and $D^{t+1}$ be represented by $1 \times 2^n$ vectors containing the joint probabilities and let the matrix A be a $2^n \times 2^n$ binary matrix defined as $$A_{ij} \begin{cases} 1, & \text{if } \exists\ x \in \{0,1\}^n, C(f_1(x), \ldots, f(x)) = j, C(x_1, \ldots, x_n) = i \\ 0, & \text{otherwise} \end{cases}$$

where $$C(i_1, \ldots, i_n) = 1 + \sum_{j=1}^{n} 2^{n-j} \cdot i_j$$

and each $i_j \in \{0,1\}$. Thus, i and j are simply indices such that i is the integer representation of the binary vector $(x_1, \ldots, x_n)$ while j encodes the binary vector $(f_1(x), \ldots, f_n(x))$. This representation is efficient because the matrix A contains exactly one non-zero entry in each row. Thus, equation (18) can be written as $$D^{t+1} = D^t \cdot A = D^0 \cdot A^{t+1}, \quad (19)$$

where $D^0 = D(x)$ is the starting (prior) joint distribution. Equation (19) is the familiar Markov chain representation, where the state-transition matrix A is binary. This is to be expected, since the state transitions are completely specified by the Boolean functions and the probability of transition can be either 0 or 1.

III. Relationship Between PBN and Bayesian Networks

Bayesian networks are graphical models that explicitly represent probabilistic relationships between variables. The model structure embeds conditional dependencies and independencies and efficiently specifies the joint probability distribution of all the variables. Recently, Bayesian network models have been used to analyze gene expression data. For that purpose, the variables in a Bayesian network typically represent expression levels of genes, but can also describe experimental conditions or unobserved variables, such as protein concentrations. The relationships between these variables are represented by a directed graph in which vertices correspond to variables and directed edges between vertices represent their dependencies. One attractive property of Bayesian networks is that they naturally allow one to select a model, from a set of competing models, that best explains the observed expression data.

On the other hand, rule-based models are appealing to biologists, since the types of dependencies between genes constitute important biological information. To partially deal with this problem, it has been suggested that annotating the edges in Bayesian networks, thus describing simple positive/negative relationships between a variable and its parent in the graph, also in the context of binary variables. A serious drawback of applying Bayesian networks to gene expression data is the computational complexity of learning the network structure. In many formulations, this is an NP-hard problem. The problem is further confounded due to the existence of equivalent networks, in the sense that they represent equivalent independence statements. Finally, standard Bayesian networks are inherently static, as they can have no directed cycles, and in order to model dynamic processes, the static model must be unrolled in time, resulting in a so-called Dynamic Bayesian Network, further complicating the process of learning the model structure and parameters.

Conversely, Boolean models encode rules of genetic regulation, are inherently dynamic, and lend themselves to tractable inference. The proposed PBN models retain these appealing properties, while furnishing the means to handle uncertainty. Let us take a closer look at the basic building blocks of PBNs and Bayesian networks, illustrating their relationships (see example 5).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary PBN of a Gene Network

Suppose we are given a PBN consisting of three genes $V=(x_1, x_2, x_3)$ and the function sets $F=(F_1, F_2, F_3)$, where $F_1=\{f_1^{(1)}, f_2^{(1)}\}$, $F_2=\{f_1^{(2)}\}$, and $F_3=\{f_1^{(3)}, f_2^{(3)}\}$. Let the functions be given by the following truth tables.

| $x_1 x_2 x_3$ | $f_1^{(1)}$ | $f_2^{(1)}$ | $f_1^{(2)}$ | $f_1^{(3)}$ | $f_2^{(3)}$ |
|---|---|---|---|---|---|
| 000 | 0 | 0 | 0 | 0 | 0 |
| 001 | 1 | 1 | 1 | 0 | 0 |
| 010 | 1 | 1 | 1 | 0 | 0 |
| 011 | 1 | 0 | 0 | 1 | 0 |
| 100 | 0 | 0 | 1 | 0 | 0 |
| 101 | 1 | 1 | 1 | 1 | 0 |
| 110 | 1 | 1 | 0 | 1 | 0 |
| 111 | 1 | 1 | 1 | 1 | 1 |
| $c_j^{(i)}$ | 0.6 | 0.4 | 1 | 0.5 | 0.5 |

Since there are 2 functions for node $x_1$, 1 function for node $x_2$, and 2 functions for node $x_3$, there are $N=4$ possible networks and matrix K is equal to $$K = \begin{bmatrix} 1 & 1 & 1 \\ 1 & 1 & 2 \\ 2 & 1 & 1 \\ 2 & 1 & 2 \end{bmatrix}$$

For example, the second row of K containing (1, 1, 2) means that the predictors $(f_1^{(1)}, f_1^{(2)}, f_3^{(3)})$ will be used. Finally, by using equation (9), the state transition matrix A is given by $$A = \begin{bmatrix} 1 & 0 & 0 & 0 & 0 & 0 & 0 & 0 \\ 0 & 0 & 0 & 0 & 0 & 0 & 1 & 0 \\ 0 & 0 & 0 & 0 & 0 & 0 & 1 & 0 \\ P_4 & P_3 & 0 & 0 & P_2 & P_1 & 0 & 0 \\ 0 & 0 & 1 & 0 & 0 & 0 & 0 & 0 \\ 0 & 0 & 0 & 0 & 0 & 0 & P_2+P_4 & P_1+P_3 \\ 0 & 0 & 0 & 0 & P_2+P_4 & P_1+P_3 & 0 & 0 \\ 0 & 0 & 0 & 0 & 0 & 0 & 0 & 1 \end{bmatrix}$$

Let us consider one of the entries in matrix A to clarify its construction. Suppose we wish to compute the transition probability $\Pr\{(1, 1, 0) \rightarrow (1, 0, 0)\}$, which corresponds to the entry $A_{7,5}$ (the indexing starts with 1). To do this, we need to use the row corresponding to $(x_1, x_2, x_3)=(1, 1, 0)$ in the network truth table given above. Then, we look for possible combinations of the predictors for each of the three genes that will give us the values (1, 0, 0). By direct inspection, one can see that either $(f_1^{(1)}, f_1^{(2)}, f_2^{(3)})$ or $(f_2^{(1)}, f_1^{(2)}, f_2^{(3)})$ result in (1, 0, 0). The two possible combinations correspond to the second and fourth rows of matrix K. That is why this transition probability is equal to $P_2+P_4$. All other entries in A are computed similarly. The state transition diagram corresponding to this matrix is shown in FIG. 5. For example, the 7th row of matrix A corresponds to (1, 1, 0) and it can be seen that the only possible transitions are to (1, 0, 0) or (1, 0, 1), corresponding to columns 5 and 6, respectively.

Example 2

Steady State Distributions of Independent PBN

To illustrate lack of a steady-state distribution, let us consider a three-variable independent PBN. Since we are not concerned with the probabilities, but only the possible Boolean functions, we can use a simplified notation to list the possible functions. We use a table consisting of eight rows corresponding to the eight states, and three columns corresponding to the possible values the Boolean functions can have for the three variables given the state determining the row. The entry * in the table means that the value of the predictor for that gene given the values of the genes in that row can be either 0 or 1. Consider the following function table:

| $x_1 x_2 x_3$ | $f^{(1)}$ | $f^{(2)}$ | $f^{(3)}$ |
|---|---|---|---|
| 000 | * | 1 | 1 |
| 001 | 0 | 1 | * |
| 010 | 0 | 0 | * |
| 011 | 0 | 0 | * |
| 100 | 1 | 1 | * |
| 101 | 1 | 1 | * |
| 110 | 1 | 0 | * |
| 111 | * | 0 | 0 |

Figure 12:
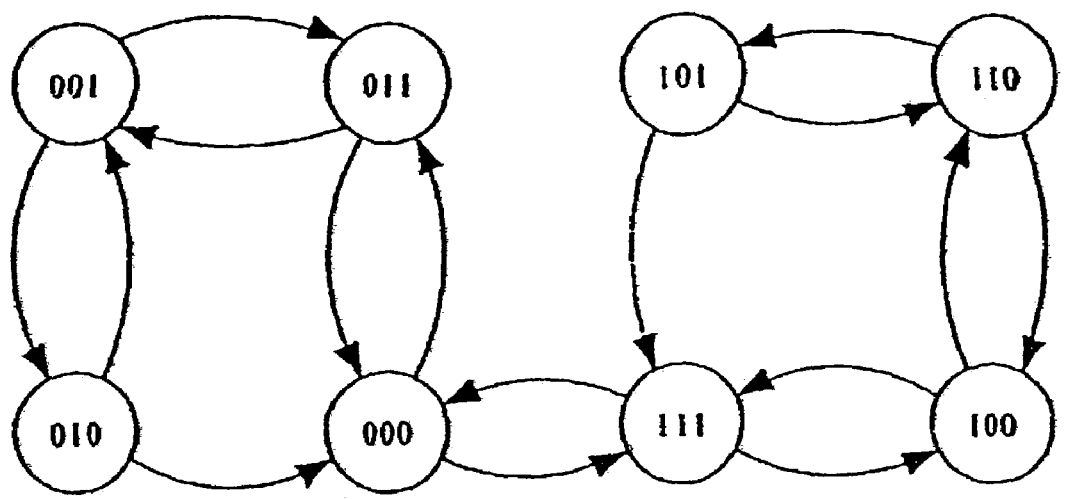
FIG. 12 illustrates an exemplary Markov diagram corresponding to steady state distributions of independent PBN of example 2.

So, for example, there are four possible predictors $f_1^{(1)}$, $f_2^{(1)}$, $f_3^{(1)}$, $f_4^{(1)}$ for the first gene. Similarly, there are 256 possible vector functions (network realizations) of the form $f=(f^{(1)}, f^{(2)}, f^{(3)})$. The corresponding Markov diagram is given in FIG. 12. Every state has period 2, and therefore the PBN is not aperiodic. Thus, there does not exist a steady-state distribution. The requirement for a PBN to possess a steady-state distribution may be imposed so that the associated long-run questions may be posed. If so, then this imposes a constraint on the collections of Boolean functions. Certain sets of Boolean functions, such as the one just considered, are not permissible.

Example 3

Steady State Distributions of Dependent PBN

The previous example considered an independent PBN. The steady-state requirement can be even more constraining for dependent PBNs. Consider the following very simple PBN with only two network functions (realizations), $f=(x_1, x_2)=(f_1^{(1)}, f_1^{(2)})=(\bar{x}_1, x_2)$ and $f=(x_1, x_2)=(f_2^{(1)}, f_2^{(2)})=(x_1, \bar{x}_2)$. Since the PBN is dependent, the selection of the predictor for the first gene may not be viewed independently of the selection of the predictor for the second gene. The above two possible network realizations imply, for instance, that if $f_1^{(1)}=\bar{x}_1$ is selected for the first gene, then $f_2^{(2)}=\bar{x}_2$, cannot be simultaneously selected for the second gene. That is, the probability that the network f takes on any realization other than the two given above, say $(f_1^{(1)}, f_2^{(2)})$, is zero.

Figure 13:
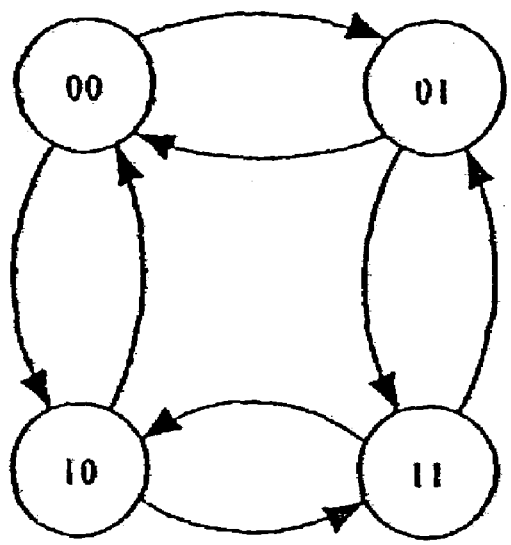
FIG. 13 illustrates an exemplary Markov diagram corresponding to steady state distributions of dependent PBN of example 3.

The corresponding Markov diagram is given in FIG. 13. This PBN is not aperiodic and does not possess a steady-state distribution. Note that the addition of the network function $f_3(x_1, x_2)=(f_3^{(1)}, f_3^{(2)})=(\bar{x}_1, \bar{x}_2)$ makes the PBN aperiodic.

Example 4

Influences of Genes in PBNS

Given Example 1 above, let $c_1^{(1)}=0.6$, $c_2^{(1)}=0.4$, $c_1^{(2)}=1$, $c_1^{(3)}=0.5$, $c_2^{(3)}=0.5$. Suppose we would like to compute the influence of variable $x_2$ on variable $x_1$. Therefore, we will need to use both of the predictors $f_1^{(1)}$ and $f_2^{(1)}$ given in the table of Example 1. Further, suppose D is the uniform distribution, that is, $D(x)=\frac{1}{8}$ for all $x \in \{0,1\}^3$. First, we get $$I_2(f_1^{(1)}) = E_D\left[\frac{\partial f_1^{(1)}(x)}{\partial x_2}\right] = 0.5$$

$$I_2(f_2^{(1)}) = E_D\left[\frac{\partial f_2^{(1)}(x)}{\partial x_2}\right] = 0.75$$

Putting these two influences together, we obtain $$I_2(x_1) = 0.5 \cdot 0.6 + 0.75 \cdot 0.4 = 0.6.$$

If we repeat these calculations between all pairs of variables, we will obtain the influence matrix $$\Gamma = \begin{bmatrix} 0.1 & 0.75 & 0.375 \\ 0.6 & 0.75 & 0.375 \\ 0.6 & 0.75 & 0.375 \end{bmatrix}$$

It is not surprising that $\Gamma$ is not symmetric, since the influence of variable $x_i$ on variable $x_j$ may be stronger than the influence of variable $x_j$ on variable $x_i$ or vice versa. Another useful measure is the average sensitivity of a function. For example, consider the sensitivity of $f$ at vector x:

$$s_x(f) = \sum_{j=1}^{n} |f(x) - f(x^{(j)})|$$

The average sensitivity of $f$ (with respect to distribution D) is then $$s_x(f) = E_D[s_x(f)] = \sum_{j=1}^{n} E_D[|f(x) - f(x^{(j)})|] = \sum_{j=1}^{n} I_j(f)$$

Thus, one definition of average sensitivity of function $f$ is the sum of the influences of all variables on $f$.

An interpretation of $s(f)$ is how much, on the average, the function $f$ changes between Hamming neighbors (i.e. those vectors differing in one coordinate). Since for PBNs, we have several predictors for each gene, we will again use the notion of influence of a gene on another gene. In other words, the average sensitivity of gene $x_i$ can be expressed as $$s(x_i) = \sum_{j=1}^{n} I_j(x_i).$$

Given the influence matrix, this can be computed as $$s(x_i) = \sum_{k=1}^{n} \Gamma_{ki}$$

Biologically, the sensitivity of a gene represents the stability or, in some sense, the autonomy of a gene. If the sensitivity of a gene is low, this implies that other genes have little effect on it. The so-called house-keeping genes that encode structural protein in the cells fall into this category. In this example, gene $x_2$ is the most sensitive.

In dealing with PBNs, one always has at least as many predictors as genes. Hence, another informative measure would be the collective effect of a gene on all the other genes. This could simply be called the influence of gene $x_i$, denoted by $r(x_i)$, and can also be obtained from the influence matrix as $$r(x_i) = \sum_{k=1}^{n} \Gamma_{ik}$$

Biologically, a gene with a high influence factor has a high collective impact on the other genes. It is precisely these genes that have the potential to regulate the dynamics of the network, as their perturbation can lead to significant downstream effects, possibly forcing the system to transition to a different basin of attraction. Many transcriptional factor genes fall into this category. In this example, genes $x_2$ and $x_3$ are equally more important than gene $x_1$.

Example 5

PBNS and Bayesian Networks

In a Bayesian network, the conditional probability of a random variable $X_i$ given all its predecessors in the graph is equal to the conditional probability of $X_i$ given only the Markovian parents of $X_i$, denoted by $Pa(X_i)$. In other words, $Pr\{x_i|x_1, \ldots, x_{i-1}\}=Pr\{x_i|Pa(x_i)\}$, where lowercase letters denote realizations of the respective random variables. Using the chain rule of probability, we can express the joint probability as a product of conditional probabilities as $$Pr\{x_1, \ldots, x_n\} = \prod_i Pr\{x_i | Pa(x_i)\}$$

This fact facilitates economical representation of joint distributions in Bayesian networks, since the entire joint distribution table does not need to be stored. Let us consider these conditional probability building blocks of Bayesian networks in the context of PBNs.

Recall that for a node (gene) $x_i$, there corresponds a set $F_i$ of possible predictor functions along with their probabilities $c_1^{(i)}, \ldots, c_{l(i)}^{(i)}$. Now, we are interested in computing the conditional probability of gene $X_i$ given its parents, namely, the set of all genes involved in predicting it. To make this more formal, let the set $X_j^{(i)} \subseteq \{x_1, \ldots, x_n\}$, $j=1, \ldots, l(i)$, denote the set of essential variables used by predictor $f_j^{(i)}$ for gene $x_i$. Then, the set $$Pa(x_i) = \bigcup_{j=1}^{l(i)} X_j^{(i)}$$

is the set of all variables used to predict gene $x_i$, or simply, the parents of $x_i$. For convenience of notation, let us expand the domains of all predictors by adding fictitious variables so that all are functions of the variables in $Pa(x_i)$. Computationally, this step is not necessary. Then, the conditional probability that $X_i=1$, given the fact that predictor $f_j^{(i)}$ is used, is equal to $$Pr\{X_i = 1 \mid f_j^{(i)} \text{ is used}\} = \sum_{x \in \{0,1\}^{|Pa(x_i)|}} D_i(x) f_j^{(i)}(x) \quad (20)$$

where $D_i(x)$ is the joint distribution over the variables in $Pa(x_i)$. Because we are in the binary setting, equation (20) can also be interpreted as the conditional expectation of $X_i$ given the predictor $f_j^{(i)}$. Computationally, we only need to consider the essential variables of $f_j^{(i)}$ and their joint distribution, which can be obtained from the entire joint distribution $D(x)$ by integrating out the fictitious variables. Moreover, equation (20) can be computed as a vector multiplication of the joint distribution and the truth table of the predictor. Ultimately, we are interested in obtaining $Pr\{X_i=1\}$. Recall that $c_j^{(i)} = Pr\{f_j^{(i)} \text{ is used}\}$. Then, $$Pr\{X_i = 1\} = \sum_{j=1}^{l(i)} Pr\{X_i = 1 \mid f_j^{(i)} \text{ is used}\} \cdot c_j^{(i)} = \sum_{j=1}^{l(i)} c_j^{(i)} \cdot \sum_{x \in \{0,1\}^{|Pa(x_i)|}} D_i(x) f_j^{(i)}(x) \quad (21)$$

Equation (11) provides the expression of the probability of the target gene $X_i$ in terms of the probabilities of the predictors and the joint distribution of the target's parent genes.

Example 6

Exemplary Glioma Sub-Network

Using human glioma gene expression data, the inventors constructed a small sub-network consisting of 15 genes. The algorithm for building a sub-network starting from a so-called "seed" gene, which uses influences of genes (Shmulevich et al., 2002a) and ensures that the sub-network functions fairly autonomously from the rest of the genes, will be described in a forthcoming paper by Hashimoto et al.

The inventors have analyzed the joint steady-state probabilities of several combinations of two genes: Tie-2 and NFκB; Tie-2 and TGFB3; and TGFB3 and NFκB. For example, for Tie-2 and NFκB, the two-state Markov chain method described above, when applied to an initial run of 10,000 iterations, produced a burn-in period of $m_0=87$ and a total number of iterations of N=48, 268. The transition probabilities α and β were both approximately equal to 0.03. The perturbation probability p was set to 0.001. When the network was ran for another 38,268 steps, the recomputed values of $m_0$ and N were 91 and 50,782, respectively. Running the network for another 3,000 iterations was sufficient for the given accuracy and the steady-state probabilities of these two genes could be determined. The steady-state probabilities for all pairs of considered genes are shown in Table 1 as percentages.

TABLE 1

Steady-state analysis of several pairs of genes

| Tie-2 | NFκB | % | Tie-2 | TGFB3 | % | TGFB3 | NFκB | % |
|---|---|---|---|---|---|---|---|---|
| OFF | OFF | 15.68 | OFF | OFF | 14.75 | OFF | OFF | 10.25 |
| OFF | ON | 41.58 | OFF | ON | 42.50 | OFF | ON | 12.47 |
| ON | OFF | 9.21 | ON | OFF | 7.96 | ON | OFF | 14.64 |
| ON | ON | 31.53 | ON | ON | 32.78 | ON | ON | 60.65 |

Tie-2 is a receptor tyrosine kinase expressed on the endothelial cells. Its two ligands, angiopoietin 1 and 2 bind Tie-2 and regulate vasculogenesis (Sato et al., 1993), an important process in embryonic development and tumor development. Other related regulators for vasculogenesis are VEGF and VERF receptors, which are often overexpressed in the advanced stage of gliomas (Cheng et al., 1997). Although no experimental evidence supports a direct transcriptional regulation of those regulators by the transcriptional factor NFκB, which is also frequently activated in glioma progression (Hayashi et al., 2001) as predicted in this analysis, the results show that NFκB, at least indirectly, influence the expression of Tie-2 expression. Thus, it may not be surprising that when NFκB is on, Tie-2 is on about 31.53/(41.58+31.53)=43% of time. Because Tie-2 is only one of the regulators for the important vasculogenesis in glioma progression, it is consistent that our analysis of long-term (steady-state) gene expression activities shows that about 40% of the time Tie-2 is on. In contrast, NFκB is on 73% of time, implying that fewer redundancies exist for NFκB activity.

Interestingly, a similar relationship exists between Tie-2 and TGFB3, as can be seen by comparing the percentages in the table. This suggests that TGFB3 and NFκB are more directly linked, which is also shown in the last three columns of the table (60% of the time, they are both on). This relationship is very likely because TGFB1, a homologue of TGFB3, was shown to have a direct regulatory relationship with NFκB (Arsura et al., 1996).

Appendix

Theorem 1: Given a PBN G(V,F) with genes V= $\{x_1, \ldots, x_n\}$ and a list F=(F1, ..., $F_n$) of sets $F_i = \{f_1^{(i)}, \ldots, f_{l(i)}^{(i)}\}$ (a) of Boolean predictors, as well as a gene mutation probability p>0.

$$A(x, x') = \left(\sum_{i=1}^{N} P_i \left[\prod_{j=1}^{n} \left(1 - |f_{K_{ij}}^{(j)}(x_1, \ldots, x_n) - x_j'|\right)\right]\right) \times (1-p)^n +$$

$$p^{\eta(x,x')} \times (1-p)^{n-\eta(x,x')} \times 1_{[x \neq x']}$$

where $$\eta(x, x') = \sum_{i=1}^{n} (x \oplus x_i')(c)$$

is the Hamming distance between vectors x and x', $P_i$ is given in equation (4) above, and $1_{[x \neq x']}$, is an indicator function that is equal to 1 only when [x≠x'].

Proof: The two terms essentially correspond to the two cases in equation (9) above. First, consider the case when no gene is mutated or equivalently, γ=(0, . . . , 0). This occurs with probability $(1-p)^n$. Thus, the next state is determined via the Boolean functions selected at that time step. The probability of transitioning from x=($x_1$, . . . , $x_n$) to x'=(x'1, . . . , $x'_n$). then, is equal to the sum of the probabilities of all network realizations $f_k$ such that $f_k(x_1, \ldots, x_n)$= ($x'_1, \ldots, x'_n$), k=1, 2, . . . , N. Thus, given that no mutation occurred.

$$A(x, x') = \sum_{i: f_i(x) = x'} P_i$$

which. in terms of the individual Boolean functions, can be expressed as:

$$\sum_{i=1}^{N} P_i \left[\prod_{j=1}^{n} \left(1 - |f_{K_{ij}}^{(j)}(x_1, \ldots, x_n) - x_j'|\right)\right]$$

where we treat binary values as real values. This is in fact the transition probability when p=0.

If at least one gene is mutated, then the transition probability depends on the number of mutated genes. Given that a mutation did occur, causing a transition from state x to state x', we can conclude that the number of mutated genes was η(x, x'), which is the Hamming distance between x and x'. Because γ∈{0,1}$^n$ is i.i.d. with E [$γ_i$]=p, i=1, . . . , n, the probability that x got changed to x' is equal to $p^{\eta(x,x')}$ X $(1-p)^{n-\eta(x,x')}$. It is clear that the fact that at least one mutation occurred implies that x and x' cannot be equal and so this expression must be multiplied by $1_{[x \neq x']}$.

Theorem 2: Let A and Ã=A−E be transition probability matrices for two irreducible Markov chains with respective stationary distributions π and π̃. Denote by $\|E\|_\infty$ the infinity-norm of E, which is the maximum over the row sums $\Sigma_j|E(i,j)|$. Let: M(x, y)=$\Sigma_k k F_k(x, y)$ denote the mean first passage time from state x to state y in the chain corresponding to A. Then, the relative change in the limiting probability for state y is $$\frac{|\pi_y - \tilde{\pi}_y|}{\pi_y} \leq \frac{1}{2}\|E\|_\infty \max_{x \neq y} M(x, y)$$

The bound is tight in the sense that there always exists a perturbation E that attains the bound, Let us now consider this result in the context of random gene perturbations.

Theorem 3 Given a PBN G(V,F) with an existing steady-state distribution, let $\pi_y$ be a limiting probability of state y when p=0 (no mutations) and let $\tilde{\pi}_y$ be the limiting probability of the same state when 0<p<½. Then, $$\frac{|\pi_y - \tilde{\pi}_y|}{\pi_y} \leq (1 - (1-p)^n) \max_{x \neq y} M(x, y)$$

Proof. The perturbation matrix E from Theorem 3 can be expressed directly from Theorem 2 as follows. Let E (x,x') be the entry in E corresponding to the transition probability from x to x', for x,x'∈{0,1}$^n$. Also, let $$A(x, x') = \sum_{i=1}^{N} P_i \left[\prod_{j=1}^{n} \left(1 - |f_{K_{ij}}^{(j)}(x_1, \ldots, x_n) - x_j'|\right)\right]$$

denote the transition matrix when p=0 and A (x,x') denote the transition matrix given in Theorem 1, where a non-zero mutation probability is assumed, In other words, $$\tilde{A}(x,x') = A(x,x') \times (1-p)^n + p^{\eta(x,x')} \times (1-p)^{n-\eta(x,x')} \times 1_{[x \neq x']} \quad (22)$$

Then. E(x,x')=A(x,x')−Ã(x,x') and for each row of E, we have $$\sum_{x'} |E(x, x')| = \quad (23)$$

$$\sum_{x'} |A(x, x') \times (1 - (1-p)^n) - p^{\eta(x,x')} \times (1-p)^{n-\eta(x,x')} \times 1_{[x \neq x']}| \leq$$

$$\sum_{x'} \left(|A(x, x') \times (1 - (1-p)^n)| + |p^{\eta(x,x')} \times (1-p)^{n-\eta(x,x')} \times 1_{[x \neq x']}|\right).$$

First, we observe that since $\Sigma_{x'} A(x,x')=1$, the first term of the summation in (23) is simply equal to $(1-(1-p)^n)$, Next, we have $$\sum_{x'} |p^{\eta(x,x')} \times (1-p)^{n-\eta(x,x')} \times 1_{[x \neq x']}| = \sum_{x' \neq x} p^{\eta(x,x')} \times (1-p)^{n-\eta(x,x')} \quad (24)$$

where we can remove the absolute value symbols since each summand is positive. Since the summation in equation (24)

is taken over all possible values of x' except x'=x, the Hamming distance η(x, x') ranges from 1 to n, As there are $$\binom{n}{k}$$

states x' that are Hamming distance k from $$x\left(\text{i.e. } |\{x' : \eta(x, x') = k\}| = \binom{n}{k}\right),$$

equation (17) can be rewritten as $$\sum_{x' \neq x} p^{\eta(x,x')} \times (1-p)^{n-\eta(x,x')} = \sum_{k=1}^{n} \binom{n}{k} p^k (1-p)^{n-k} = 1 - (1-p)^n \quad (25)$$

Thus, every row of E satisfies $$\sum_{x'} |E(x, x')| \leq 2(1 - (1-p)^n)$$

and so $$\|E\|_\infty \leq 2(1-(1-p)^n) \quad (26)$$

as well,

Using (26) together with Theorem 2 gives the desired result.

Theorem 3 allows us to bound the sensitivity of the limiting probabilities of any state of the PBN, relative to the probability of random gene perturbation, The mean first passage times M(x,y) can be computed in a straightforward way by using the recursive formula in (10), The same type of analysis as above may be conducted between two PBNs with different mutation probabilities $p_1 < p_2$ and the relative sensitivity of the limiting probabilities can be expressed in terms of $p_1$, $p_2$, and the mean first passage times. One important implication of Theorem 3 is that if a particular state of a PBN can be "easily reached" from other states, meaning that the mean first passage times are small, then its steady-state probability may be relatively unaffected by perturbations. Such sets of states, if we hypothesize them to correspond to some functional cellular states, are thus relatively insensitive to random gene mutations.

What is claimed is:

1. A method for constructing a model network comprising:
   (a) obtaining measurements of factors that influence a value of a node in a network;
   (b) determining a measure of association between a combination of network nodes associated with at least one other network node;
   (c) constructing a plurality of predictor functions for the at least one other network node given the combination of network nodes;
   (d) transforming the measure of association between the combination of network nodes and at least one other network node into a predictor function probability; and
   (e) constructing a network representative of a complex system utilizing the plurality of predictor functions and the predictor function probabilities.

2. The method of claim 1, wherein the network is representative of a biological system.

3. The method of claim 2, wherein the biological system is an animal.

4. The method of claim 2, wherein the biological system is a cell.

5. The method of claim 2, wherein the biological system is a gene regulatory network.

6. The method of claim 1, wherein at least one predictor function is based on multivariate logic.

7. The method of claim 6, wherein at least one predictor function is based on ternary logic.

8. The method of claim 1, wherein at least one predictor function is based on binary logic.

9. A method for constructing a network representative of a biological system comprising:
   (a) obtaining measurement of factors in a biological system that influence a value of a node in a network;
   (b) selecting a combination of network nodes associated with a state of at least one other network node;
   (c) determining a measure of association between the combination of network nodes and at least one other network node;
   (d) constructing a plurality of predictor functions for a value of at least one other network node given the combination of network nodes;
   (e) transforming the measure of association between the combination of network nodes and the at least one other network node into a predictor function probability; and
   (f) constructing a network representative of a biological system utilizing the plurality of predictor functions and the predictor function probabilities.

10. The method of claim 9, wherein the biological network is a gene regulatory network.

11. The method of claim 9, wherein selecting a combination of network nodes comprises identifying at least one sub-cluster of nodes.

12. The method of claim 11, further comprising selecting meta-clusters of nodes, wherein the meta-cluster is a cluster of sub-clusters.

13. An apparatus comprising a machine readable medium containing instructions which, when executed by a machine, cause the machine to perform operations comprising:
   (a) receiving values for a plurality of network nodes;
   (b) selecting a combination of network nodes associated with a state of at least one other network node;
   (c) determining a cumulative measure of association between the combination of network nodes and at least one other network node;
   (d) constructing a plurality of predictor functions for a value of at least one other network node given the combination of network nodes;
   (e) transforming the cumulative measure of association between the combination of network nodes and at least one other network node into a predictor function probability; and
   (f) constructing a network representative of a complex system utilizing the plurality predictor functions and the predictor function probabilities.

14. The apparatus of claim 13, further comprising sending the result of the performed operations to a remote user.

15. The apparatus of claim 14, wherein sending is by using internet compatible protocols.

16. A method comprising:
(a) identifying a plurality of network nodes related to a state of at least one other network node within a network, wherein each network node of the network includes a network node value which influences a gene expression state;
(b) obtaining measurements of factors that influence a value of at least one network node;
(c) constructing a plurality of predictor functions from a combination of network nodes utilizing at least one of the network node values for at least one target node;
(d) determining a cumulative measure of association for combinations of network nodes;
(e) transforming the cumulative measure of association into a probability that any one of a plurality of predictor functions is utilized to determine a state of at least one other node of a network; and
(f) connecting a plurality of network node combinations to construct a probabilistic Boolean network.

17. The method of claim 16, wherein the network is a biologic network.

18. The method of claim 16, wherein identifying a plurality of network nodes comprises identifying a sub-cluster of nodes.

19. The method of claim 18, further comprising identifying meta-clusters of nodes, wherein the meta-cluster is a cluster of sub-clusters.

20. The method of claim 17, further comprising diagnosing a disease state using the probabilistic Boolean network.

21. The method of claim 17, further comprising identifying a therapeutic target using the probabilistic Boolean network.

* * * * *